United States Patent
Takemoto

(10) Patent No.: US 10,463,809 B2
(45) Date of Patent: Nov. 5, 2019

(54) PROTECTION DEVICE AND MEDICAL DEVICE ASSEMBLED BODY

(71) Applicant: TERUMO KABUSHIKI KAISHA, Tokyo (JP)

(72) Inventor: Masafumi Takemoto, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 276 days.

(21) Appl. No.: 15/663,330

(22) Filed: Jul. 28, 2017

(65) Prior Publication Data

US 2018/0015233 A1 Jan. 18, 2018

Related U.S. Application Data

(63) Continuation of application No. PCT/JP2016/052669, filed on Jan. 29, 2016.

(30) Foreign Application Priority Data

Jan. 30, 2015 (JP) .................................. 2015-017214

(51) Int. Cl.
*A61M 5/32* (2006.01)
*A61M 5/00* (2006.01)

(52) U.S. Cl.
CPC .......... *A61M 5/3271* (2013.01); *A61M 5/002* (2013.01); *A61M 5/32* (2013.01); *A61M 5/326* (2013.01); *A61M 5/3245* (2013.01); *A61M 5/3272* (2013.01)

(58) Field of Classification Search
CPC .............. A61M 5/3269; A61M 5/3271; A61M 5/3272; A61M 2005/3267
See application file for complete search history.

(56) References Cited

U.S. PATENT DOCUMENTS

| 8,128,594 B1 * | 3/2012 | Chang ................. A61M 5/3272 604/110 |
| 9,352,099 B2 * | 5/2016 | Roberts ................. A61M 5/326 |
| 2008/0167611 A1 | 7/2008 | Miller |

(Continued)

FOREIGN PATENT DOCUMENTS

| JP | 4981030 | 4/2012 |
| JP | 2013-529987 | 4/2013 |
| JP | 2014-530051 | 11/2014 |

(Continued)

OTHER PUBLICATIONS

International Search Report issued in International Patent Application No. PCT/US2016/052669 dated Apr. 5, 2016.

*Primary Examiner* — Laura A Bouchelle
(74) *Attorney, Agent, or Firm* — Foley & Lardner LLP

(57) ABSTRACT

A protection device is attachable to a syringe that includes a needle. The protection device includes an inner cylinder having a cam structure with at least one protrusion; an outer cylinder that covers the inner cylinder and the needle; and a spring. The outer cylinder has a guiding path structure including at least one guiding path. The guiding path structure includes an elastic member allowing the cam structure to move; and an inner edge provided at a position in a peripheral wall of the outer cylinder different from the elastic member. The inner edge is configured to regulate movement of the cam structure by engaging with the cam structure.

17 Claims, 20 Drawing Sheets

(56) References Cited

U.S. PATENT DOCUMENTS

2011/0319832 A1 12/2011 Chun
2015/0190586 A1 7/2015 Takemoto

FOREIGN PATENT DOCUMENTS

| WO | WO-2006/131832 | 12/2006 |
| WO | WO-2012/000834 | 1/2012 |
| WO | WO-2013/041641 | 3/2013 |
| WO | WO-2013/134465 | 9/2013 |
| WO | WO-2015/022787 | 2/2015 |

* cited by examiner

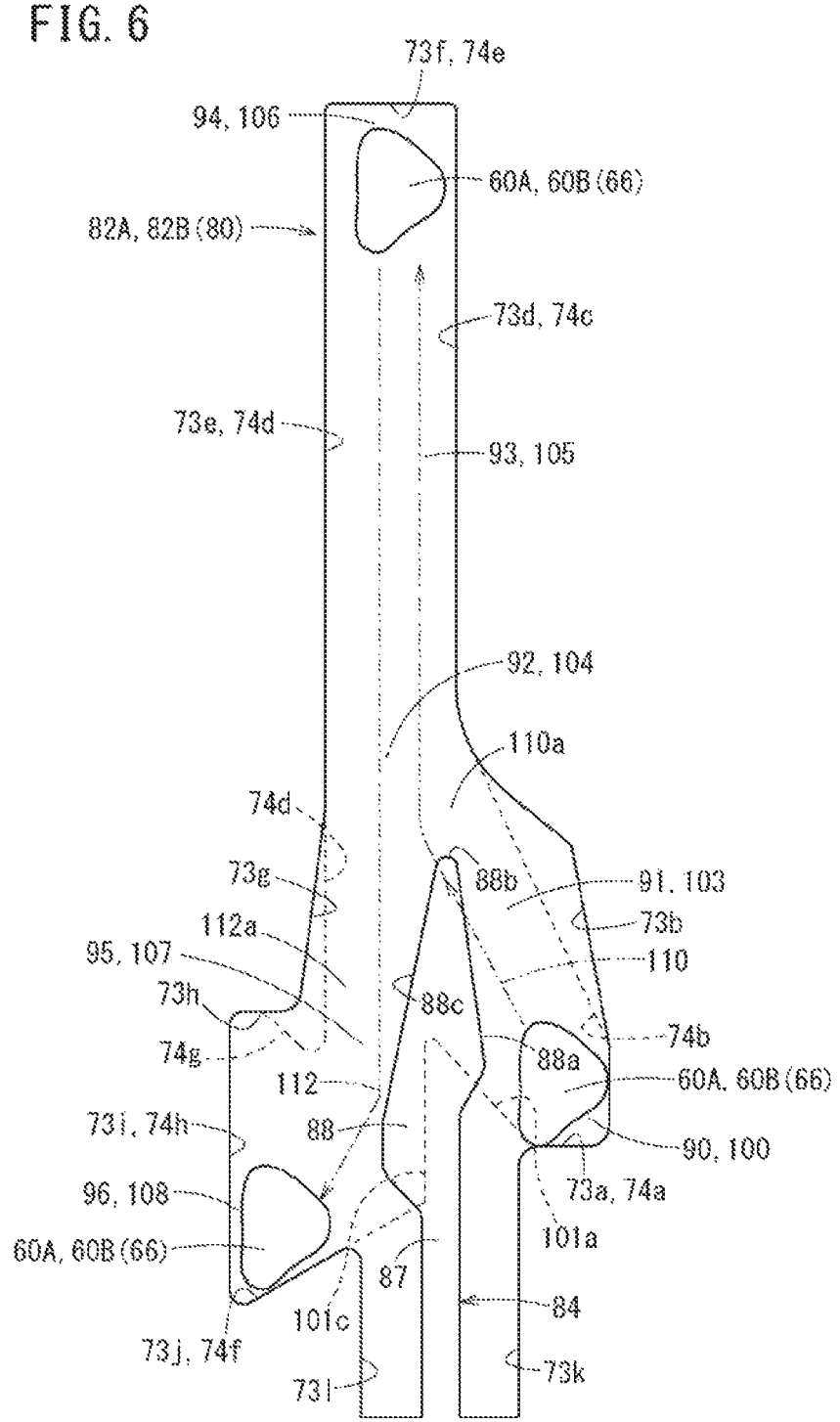

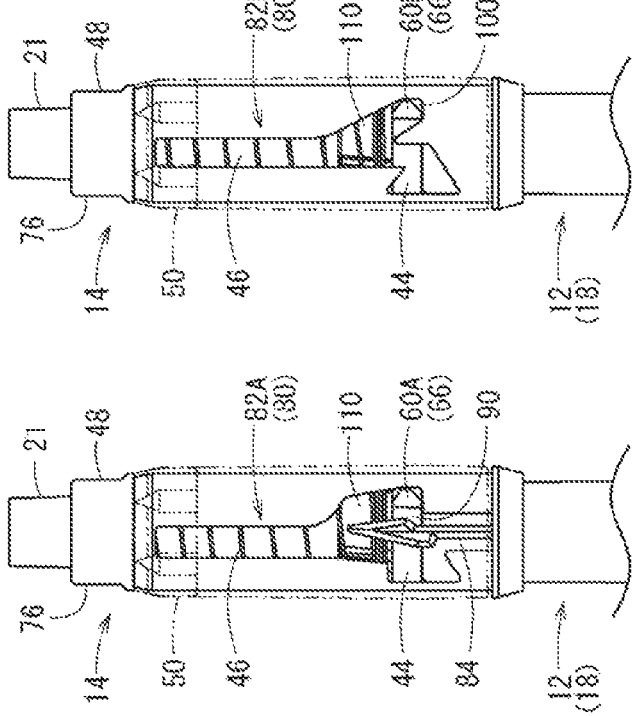

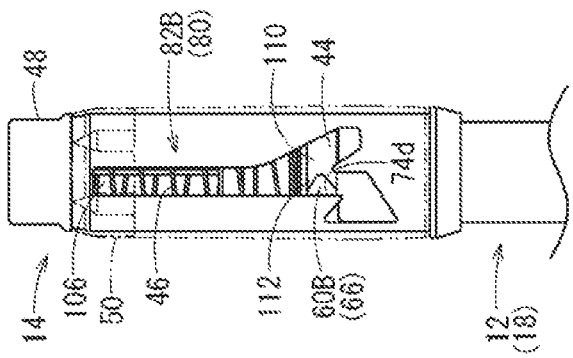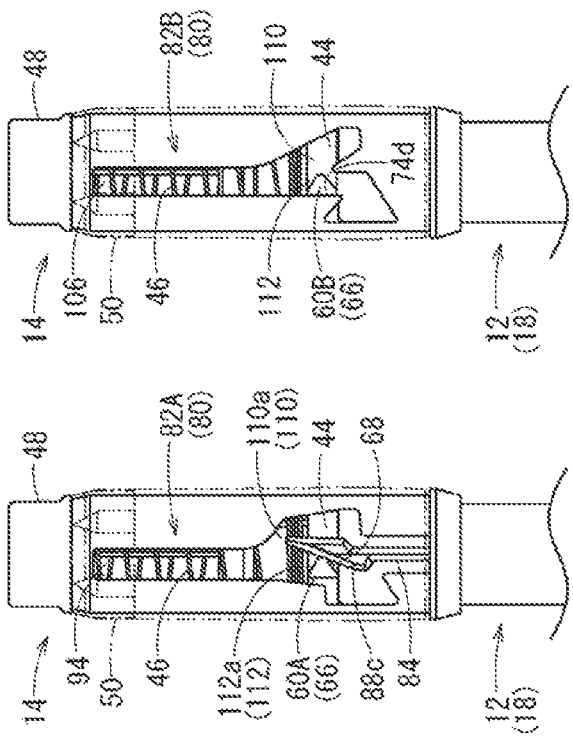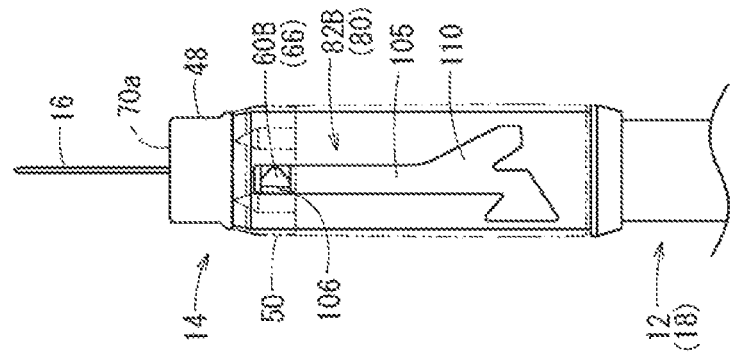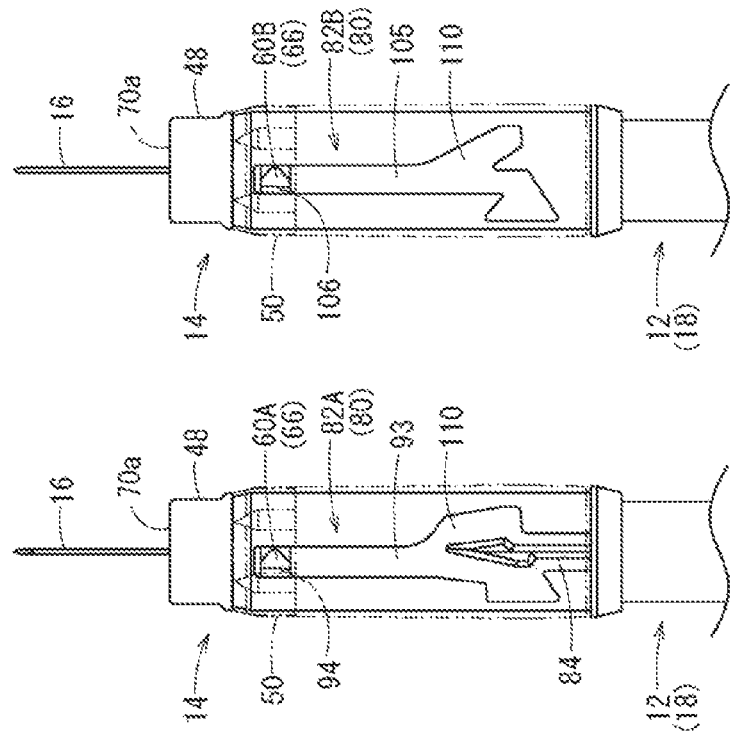

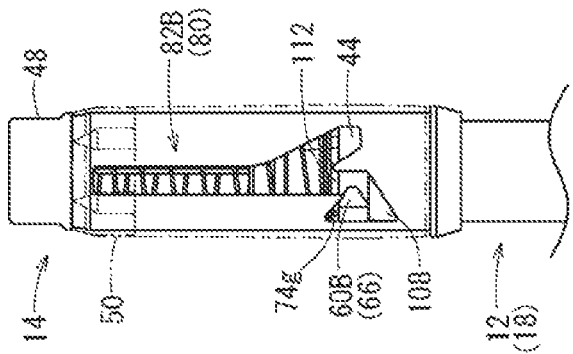
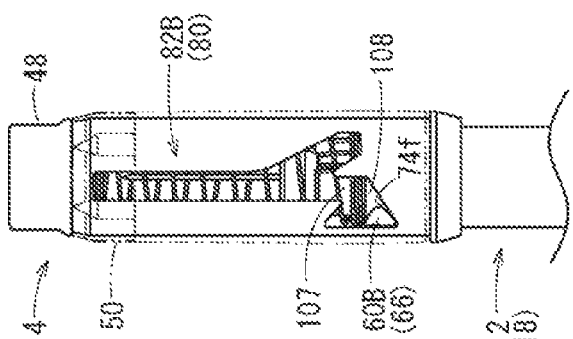
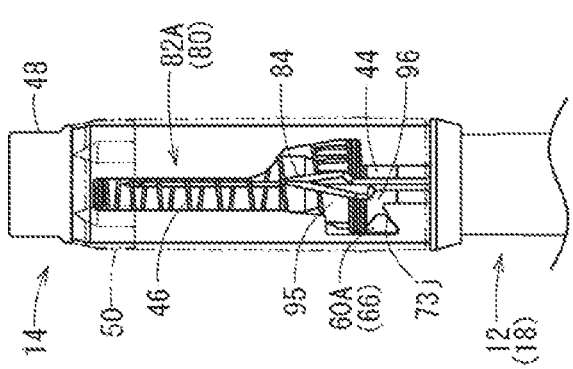

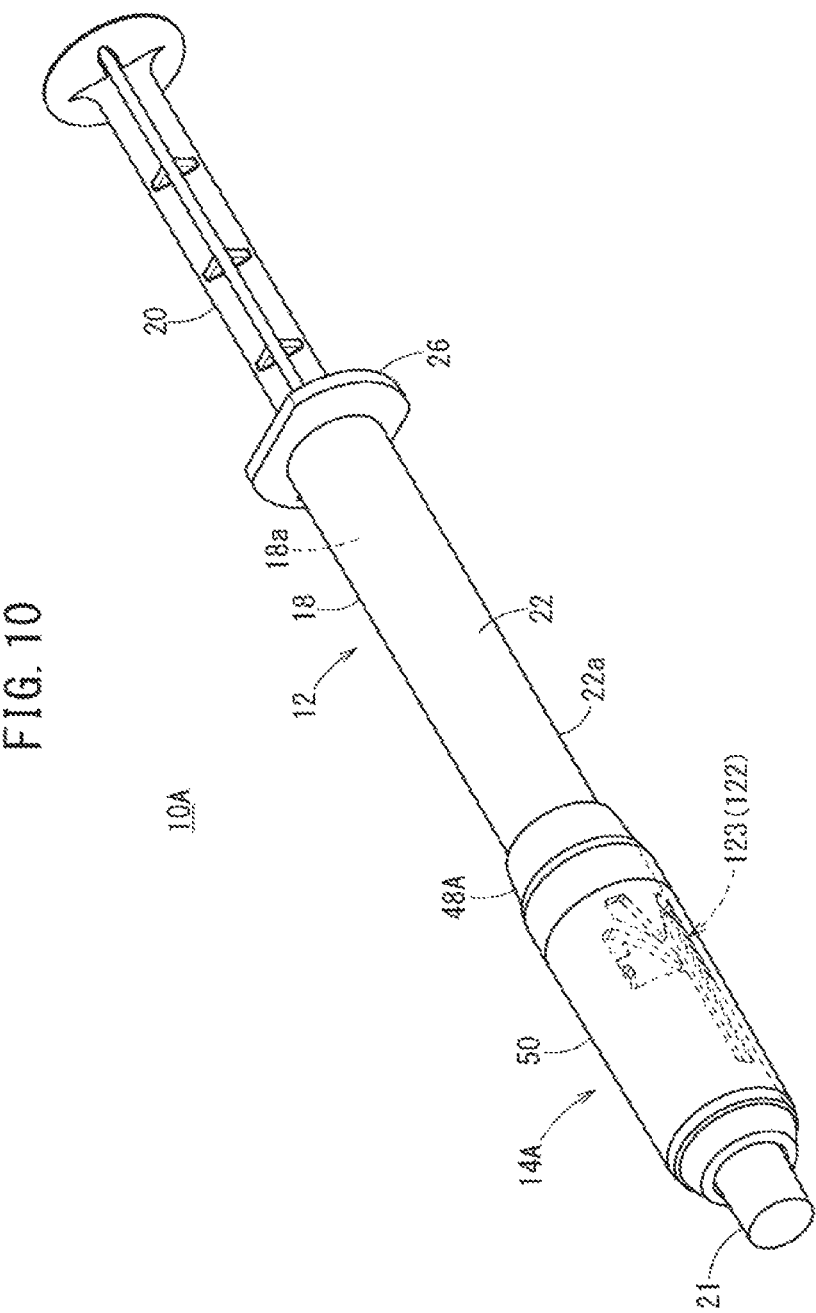

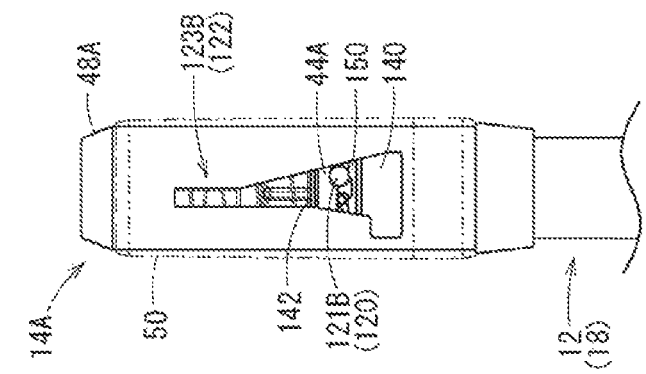
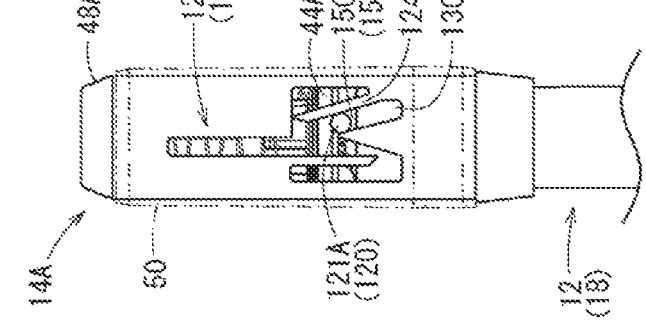
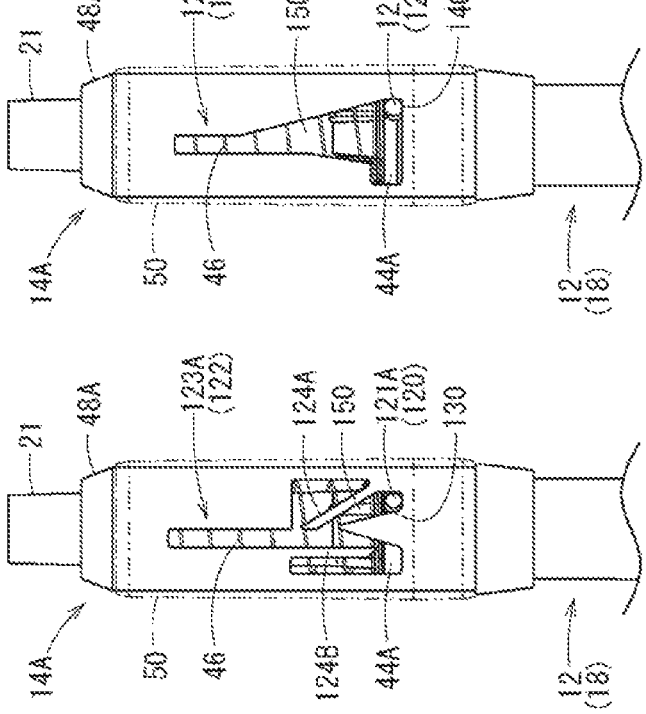

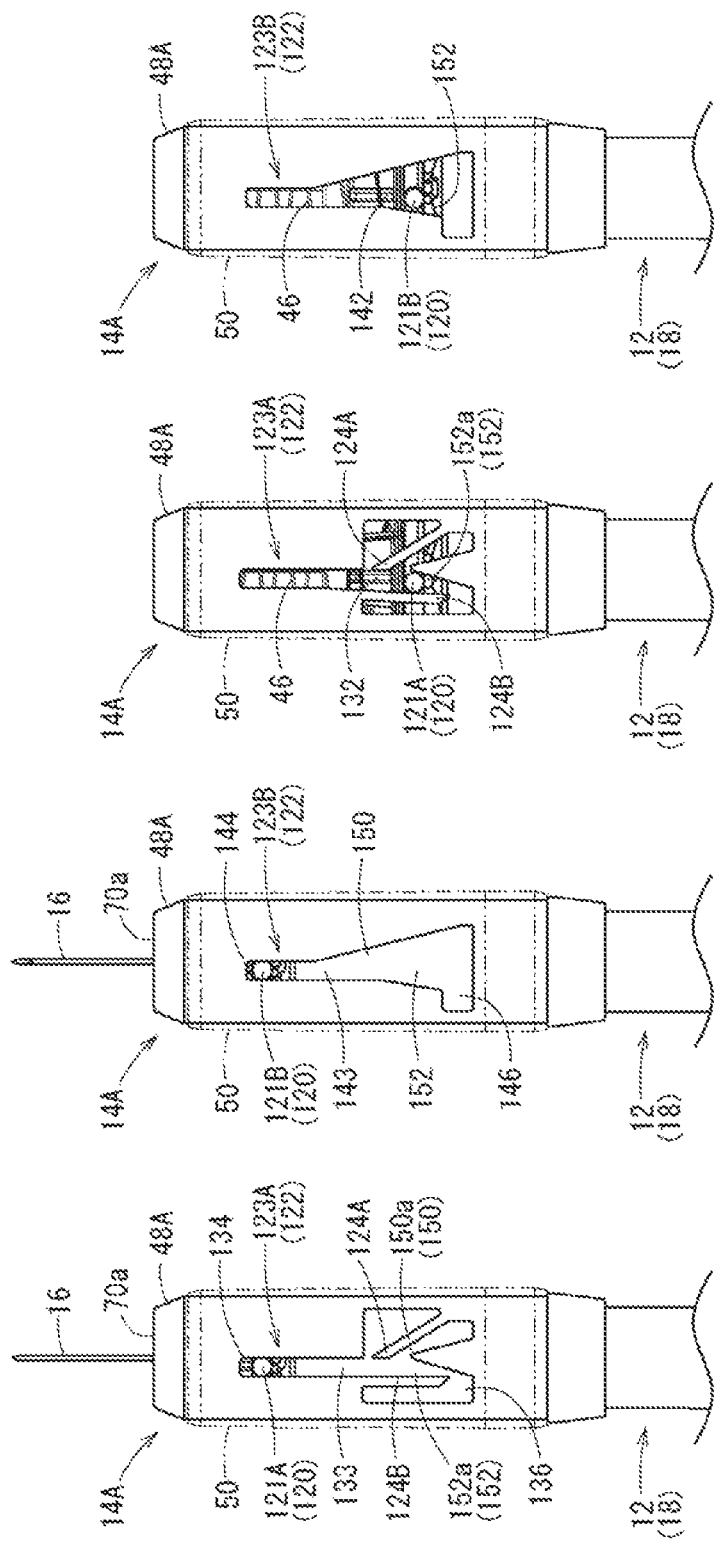

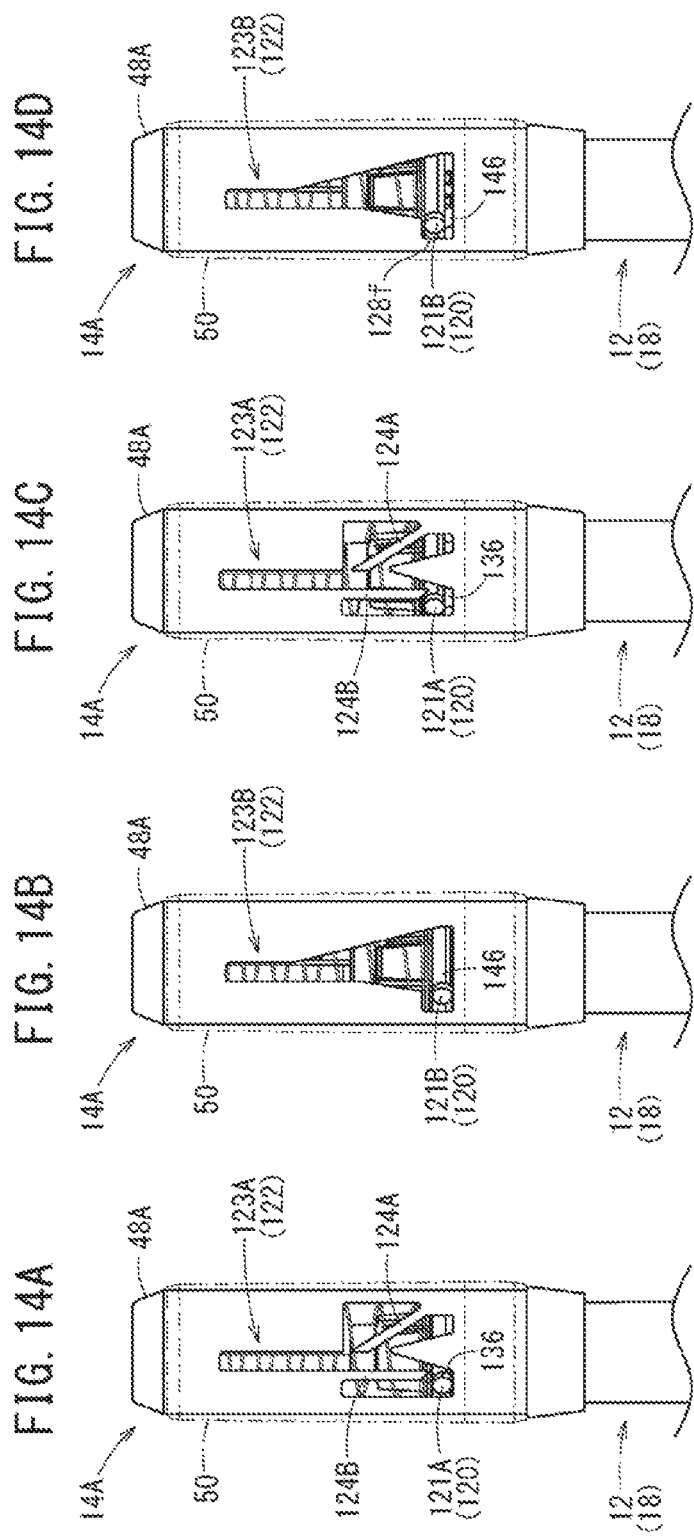

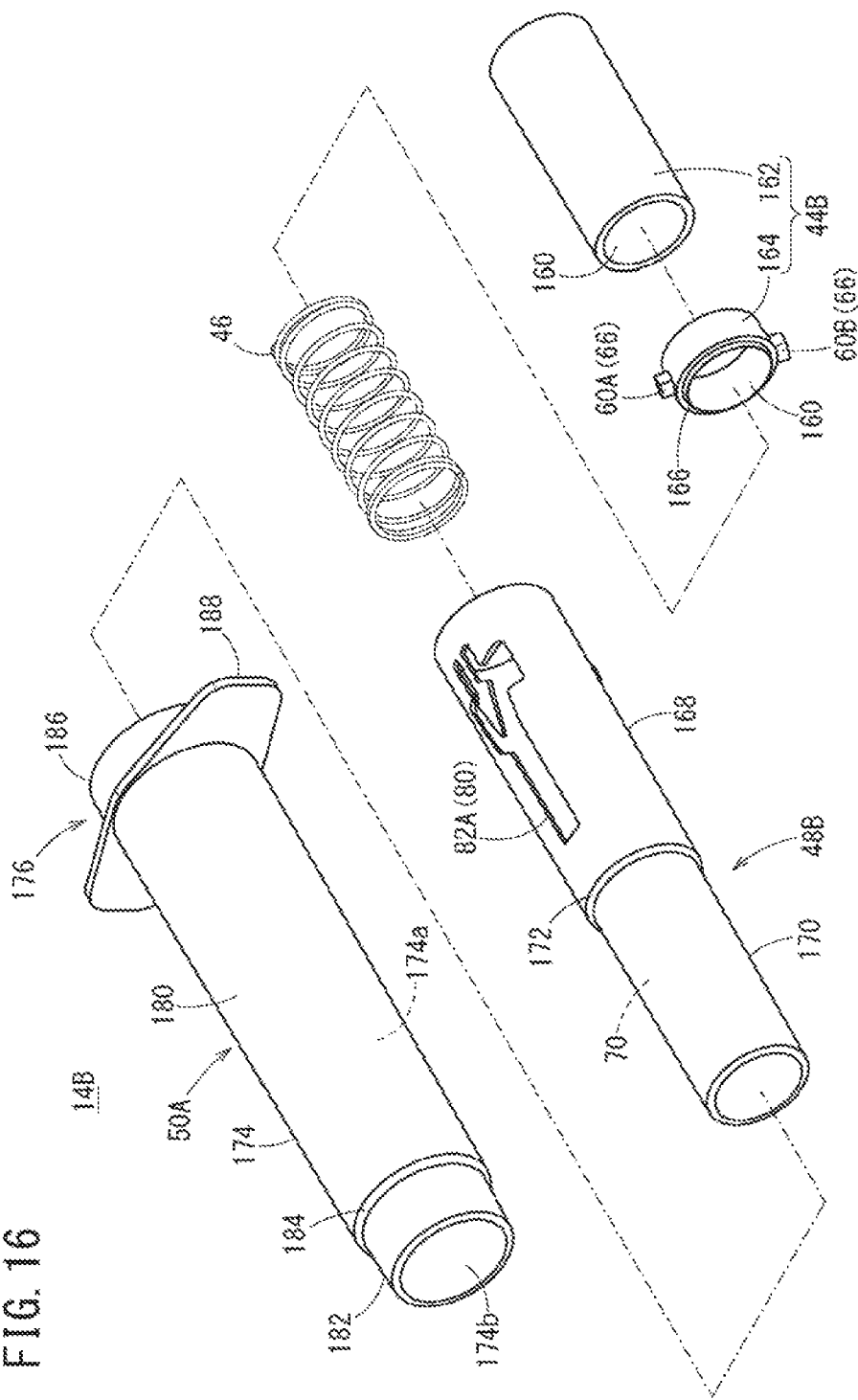

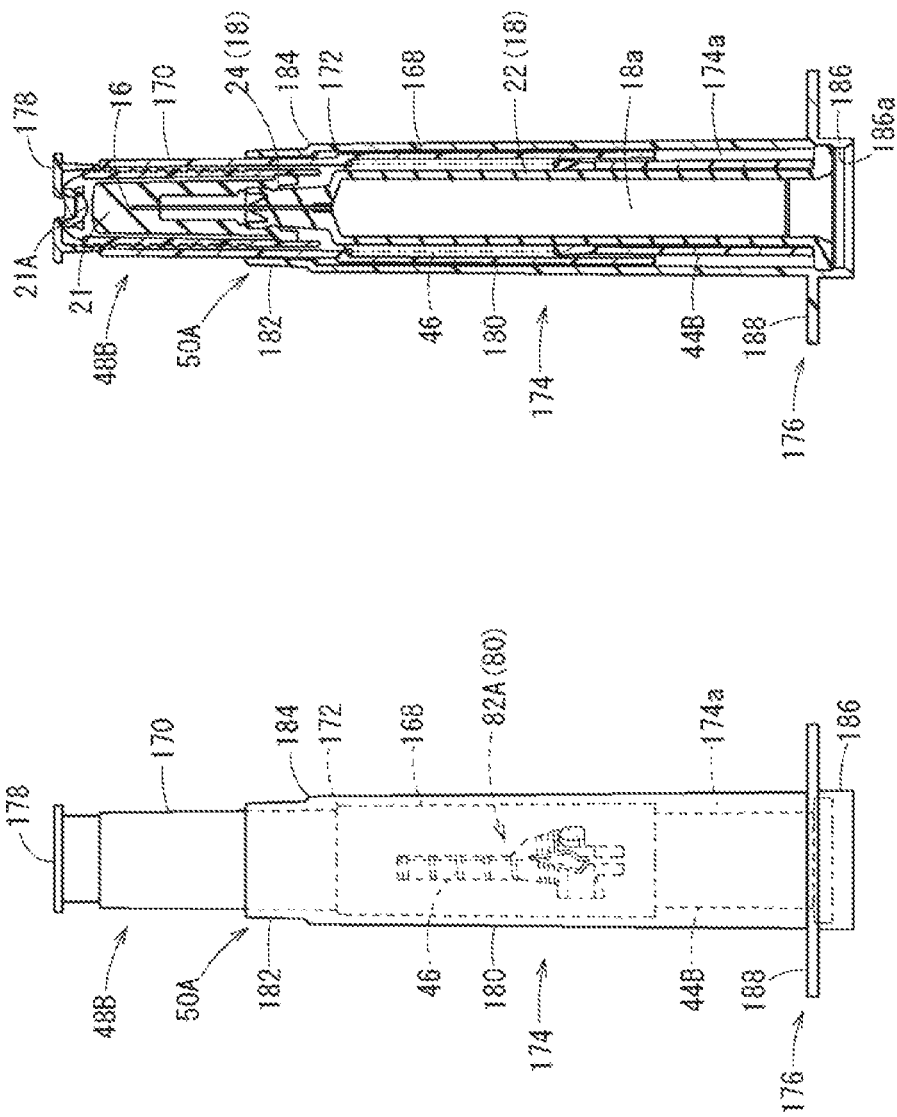

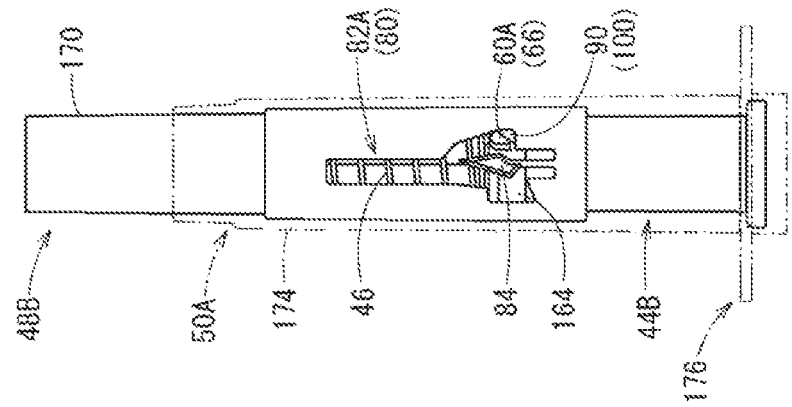
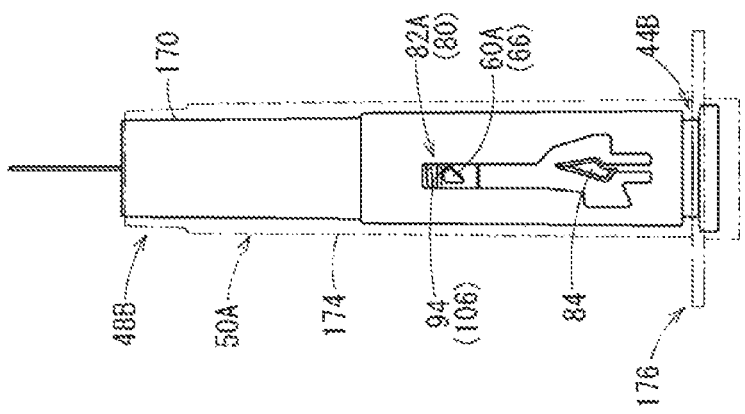
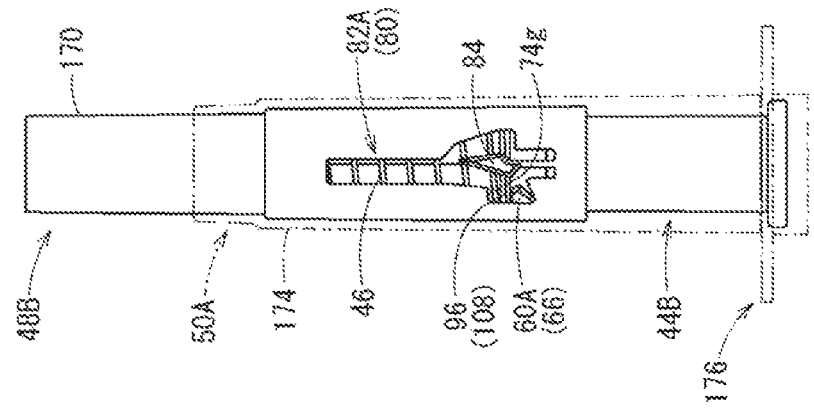

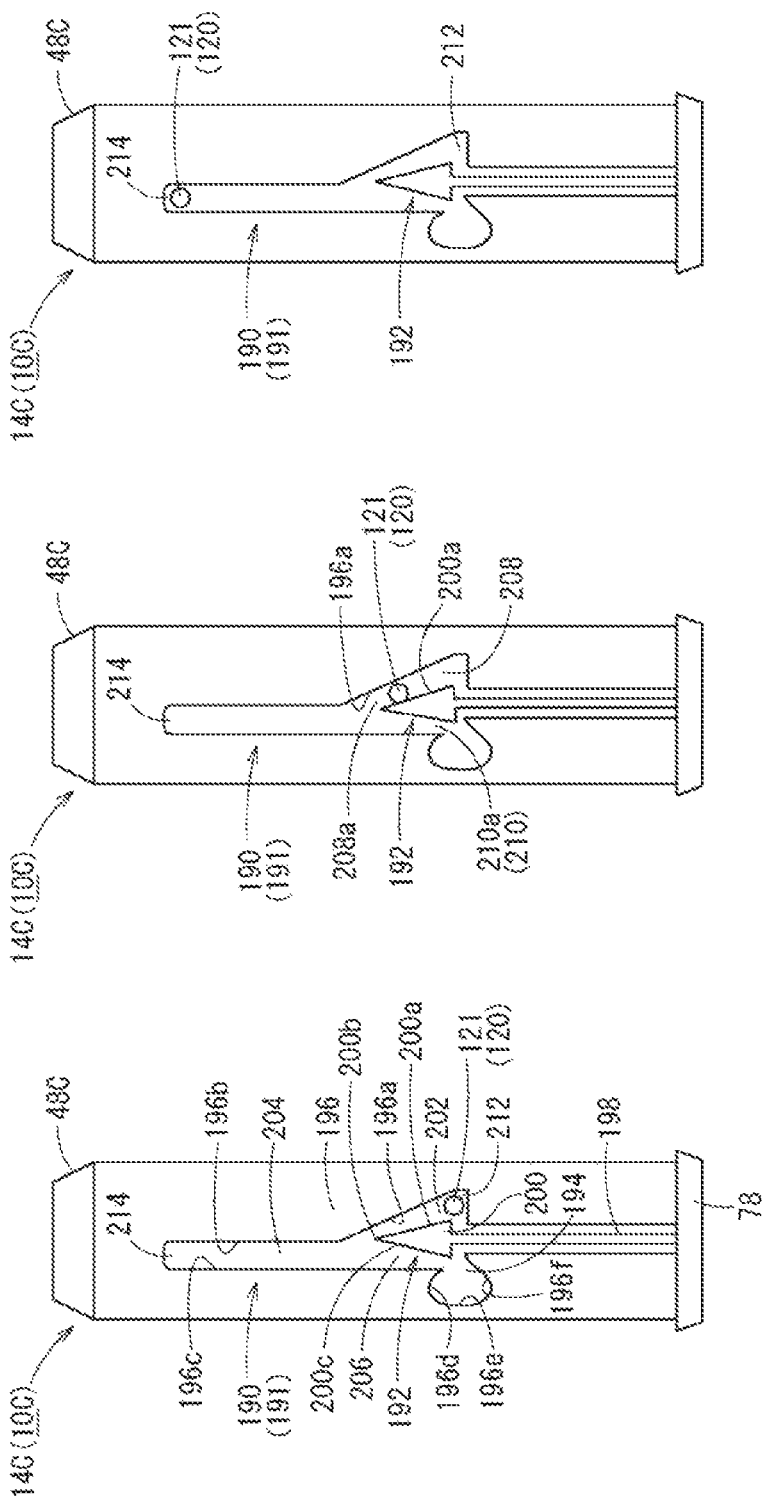

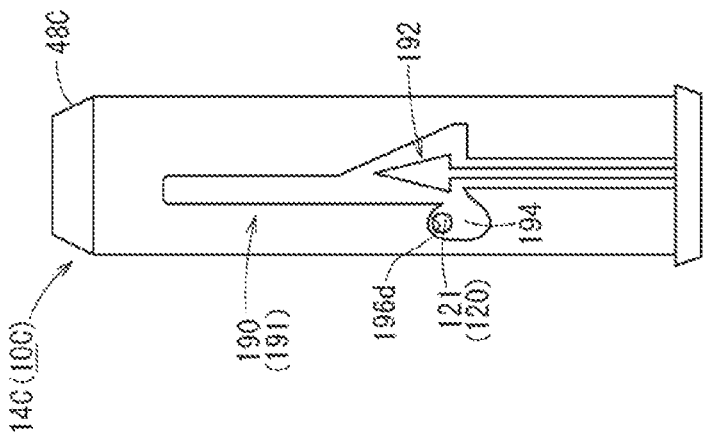
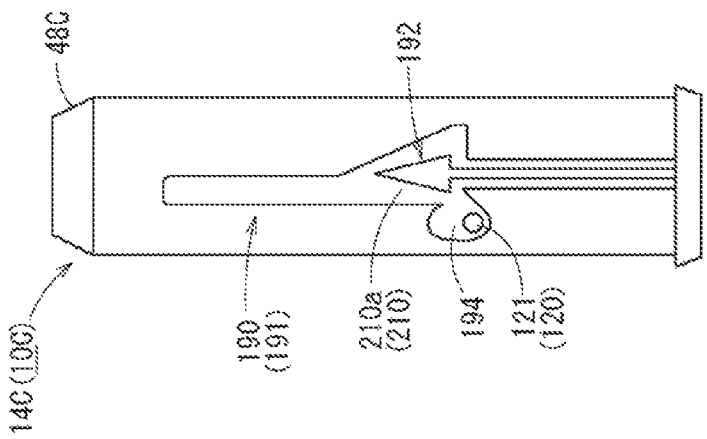
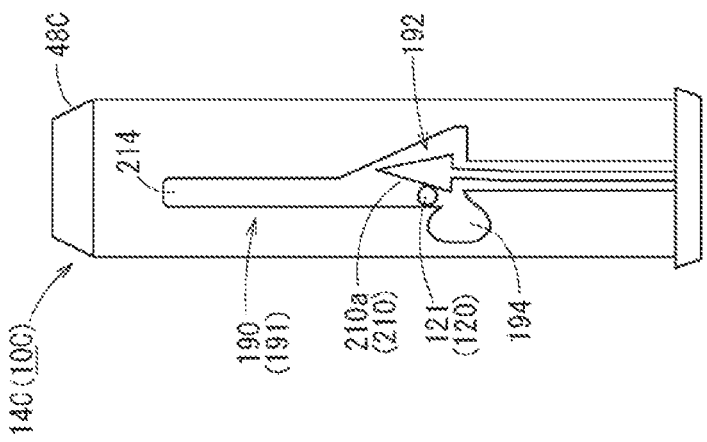

PROTECTION DEVICE AND MEDICAL DEVICE ASSEMBLED BODY

CROSS-REFERENCE TO RELATED APPLICATIONS

This application is a bypass continuation of PCT Application No. PCT/JP2016/052669, filed on Jan. 29, 2016, which claims priority to Japanese Application No. 2015/017214, filed on Jan. 30, 2015. The contents of both of these applications are hereby incorporated by reference in their entireties.

BACKGROUND

The present disclosure relates to a protection device that covers a needle tip after puncturing a target of puncture with a needle, and a medical device assembled body attached with this protection device.

In a syringe used for injecting a patient, one provided with a protection device (medical device assembled body) has been developed to prevent inadvertent puncture of a needle after puncturing.

For example, a protection device disclosed in JP 4981030 A includes an inner member (supporting body) having a needle; and an outer cylinder (sleeve) disposed outside the inner member and relatively movable with respect to the inner member. In this case, a flexible tab is provided at a predetermined position closer to a proximal end of the inner member. The flexible tab extends in a distal end direction, and a distal end of the flexible tab is formed with a protrusion (peg). The outer cylinder includes a guiding path (traveling path) having a U-shape, configured to receive the protrusion of the inner member; and an elastic member (step) protruded from a peripheral wall toward a lock position in the guiding path.

At the time of puncturing with the needle, this protection device advances the inner member with respect to the outer cylinder so as to expose the needle from a distal end. At this time, the protrusion disposed in the guiding path is displaced to a puncture position at a distal end of the guiding path. After puncturing, the outer cylinder is pushed in the distal end direction by an internal spring so that the outer cylinder covers the needle. Accordingly, the protrusion is displaced along the guiding path in a proximal end direction, passing over a narrowed portion of the guiding path including the elastic member, thereafter being disposed in the lock position on a side closer to the proximal end. Even when a force to re-expose the needle (the receding movement of the outer cylinder) is applied to this lock position, the protrusion is caught in the elastic member so that exposure of the needle is avoided.

SUMMARY

In the above-described type of a protection device, when an outer cylinder recedes with strong force with respect to an inner member, a catch between an elastic member and a protrusion is released and a needle is re-exposed. In order to prevent such re-exposure of the needle, it is conceivable to enhance rigidity of the elastic member so that the protrusion (a cam structure) firmly gets caught in the elastic member. However, simple enhancement of the rigidity of the elastic member increases the possibility of the protrusion not passing over the elastic member when moving to a lock position, which fails to avoid the re-exposure of the needle. In other words, the elastic member in the conventional protection device has both a function of allowing the passage of the protrusion and a function of regulating a movement of the protrusion at the lock position, which weakens the force to prevent the re-exposure of the needle and can reduce safety.

Certain embodiments described in this disclosure have been made in light of the aforementioned findings, and one object of certain embodiments is to provide a protection device and a medical device assembled body configured to inhibit re-exposure of a needle by smoothly moving a cam structure to a lock position after puncturing with the needle and by firmly preventing the cam structure guided to the lock position from being detached from the lock position.

According to one embodiment, a protection device is provided. The protection device is configured to be attached to a medical device that includes a needle having a needle tip at a distal end thereof and a needle holder holding the needle. The protection device is configured to cover the needle tip after puncturing a target of puncture with the needle. The protection device includes: an inner member rotatably disposed at an outside of the medical device in a circumferential direction, and having a cam structure that includes at least one protrusion protruded outward in a radial direction; an outer cylinder configured to cover at least a part of the needle and an outside of the inner member before puncturing; and a biasing member configured to bias the outer cylinder with respect to the inner member in a distal end direction. The outer cylinder includes a guiding path structure that includes at least one guiding path, the at least guiding path receiving the cam structure and rotating the inner member in accordance with relative movement of the outer cylinder, the outer cylinder moving relative to the inner member in a proximal end direction at the time of puncturing so as to expose the needle tip and moving relative to the inner member in the distal end direction after puncturing so as to cover the needle tip by biasing force, wherein the guiding path structure includes: an initial position where the cam structure is disposed before puncturing; a puncture position disposed at distal of the initial position, where the cam structure is to move at the time of puncturing; a lock position disposed at proximal of the puncture position, where the cam structure is to move after puncturing; a distal-end-directional path that guides the cam structure from the initial position to the puncture position at the time of puncturing; a proximal-end-directional path that guides the cam structure from the puncture position to the lock position after puncturing; a proximal-end-directional-path elastically-deformable portion that forms a proximal-end-directional-path narrowed portion together with an edge of the proximal-end-directional path in a middle region of the proximal-end-directional path, the proximal-end-directional-path narrowed portion having a width smaller than a width of the protrusion in the proximal-end-directional path, the proximal-end-directional-path elastically-deformable portion being configured to deform elastically upon contacting with the protrusion so as to increase the width of the proximal-end-directional-path narrowed portion and allow the cam structure to move from the puncture position to the lock position; a proximal-end-directional-path rotation-inducing portion that is configured to induce the inner member to rotate relative to the outer cylinder by contacting with the cam structure when the protrusion passes over the proximal-end-directional-path narrowed portion path (112a, 152a, 210a) and moves to the lock position due to the biasing force of the biasing member; and a regulating portion that is disposed at a position different from the proximal-end-directional-path elastically-deformable portion in a peripheral wall of the outer cylinder, the regulating portion being configured to inhibit movement of the cam structure in the distal end direction with respect to the outer cylinder by engaging with the cam structure disposed in the lock position, wherein the proximal-end-directional-path elastically-deformable portion is configured to inhibit rotation of the inner member with respect to the outer cylinder by contacting with the cam structure when the cam structure moves from the lock position toward the proximal-end-directional-path narrowed portion.

According to the above, the protection device can preferably prevent the re-exposure of the needle after puncturing with the needle since the guiding path structure of the outer cylinder has the proximal-end-directional-path elastically-deformable portion and the regulating portion at different positions. In other words, the proximal-end-directional-path elastically-deformable portion elastically deforms by contacting with the cam structure moving along the proximal-end-directional path, allowing the cam structure to pass through the proximal-end-directional-path narrowed portion so as to smoothly guide the cam structure to the lock position. The regulating portion opposing the cam structure at the lock position is formed separately from the proximal-end-directional-path elastically-deformable portion, which enhances rigidity and firmly inhibits detachment of the cam structure from the lock position even when acting force is applied from the cam structure. Furthermore, the proximal-end-directional-path elastically-deformable portion can inhibit rotation of the inner member by contacting with the cam structure disposed in the lock position, thereby preventing disengagement between the cam structure and the regulating portion at the lock position.

In this case, it is preferable that the proximal-end-directional-path elastically-deformable portion is elastically deformable by contacting with the protrusion so as to allow the protrusion to pass through the proximal-end-directional-path narrowed portion substantially linearly along an axis of the outer cylinder.

In this manner, since the proximal-end-directional-path elastically-deformable portion is allowed to pass through the protrusion substantially linearly, it is possible to prevent friction when the cam structure moves along the proximal-end-directional path. Accordingly, it is possible to weaken the biasing force of the biasing member, which facilitates the puncturing operation with the needle.

It is preferable that the proximal-end-directional path is configured to guide the cam structure so as to allow the cam structure to move substantially linearly along the axis of the outer cylinder from the puncture position to the proximal-end-directional-path rotation-inducing portion.

In this manner, as the cam structure is allowed to move linearly by the proximal-end-directional path, it is possible to further prevent the friction between the cam structure and the proximal-end-directional path so that the biasing force of the biasing member can be weakened.

Furthermore, it is preferable that the guiding path structure has a distal-end-directional-path rotation-inducing portion in the that is disposed at a middle region of the distal-end-directional path and is configured to induce the inner member to rotate relative to the outer cylinder by contacting with the cam structure when the cam structure moves from the initial position to the puncture position.

In this manner, since the guiding path structure includes the distal-end-directional-path rotation-inducing portion, it is possible to rotate the inner member at the time of puncturing and to prevent the cam structure from returning to the initial position.

Still further, the proximal-end-directional-path elastically-deformable portion is formed as only one in the outer cylinder.

In this manner, since the proximal-end-directional-path elastically-deformable portion is formed as only one in the outer cylinder, the cam structure receives less repulsion from the proximal-end-directional-path elastically-deformable portion when passing through the proximal-end-directional-path narrowed portion so that the cam structure can reliably pass through the proximal-end-directional-path narrowed portion.

Herein, it is preferable that the guiding path structure includes a first guiding path and a second guiding path that is disposed at a position different from the first guiding path in the peripheral wall of the outer cylinder, the cam structure includes a first protrusion that moves inside the first guiding path and a second protrusion that moves inside the second guiding path, the proximal-end-directional-path elastically-deformable portion is formed in the first guiding path, and the regulating portion is formed in the second guiding path, wherein each of the initial position, the puncture position, the lock position, the distal-end-directional path, and the proximal-end-directional path is formed by the first guiding path and the second guiding path.

In this manner, since the guiding path structure includes the proximal-end-directional-path elastically-deformable portion in the first guiding path and the regulating portion in the second guiding path, the proximal-end-directional-path elastically-deformable portion acts with respect to the first protrusion received in the first guiding path, and the regulating portion acts with respect to the second protrusion received in the second guiding path. Accordingly, the inner member as the whole cam structure is guided to the lock position and prevented from being detached from the lock position, which preferably prevents the re-exposure of the needle.

Furthermore, it is preferable that the guiding path structure includes an distal-end-directional-path elastically-deformable portion that forms a distal-end-directional-path narrowed portion together with an edge of the distal-end-directional path in a middle region of the distal-end-directional path, the distal-end-directional-path narrowed portion having a width smaller than a width of the cam structure in the distal-end-directional path, wherein the distal-end-directional-path elastically-deformable portion is configured to deform elastically upon contacting with the cam structure so as to increase the width of the distal-end-directional-path narrowed portion and prevent the cam structure from moving from the puncture position to the initial position.

In this manner, even though the protection device is provided with the distal-end-directional-path narrowed portion having the width smaller than the protrusion between the edge of the distal-end-directional path, the cam structure makes the distal-end-directional-path elastically-deformable portion deform elastically when moving through the distal-end-directional path so that the cam structure can smoothly pass through the distal-end-directional-path narrowed portion. After passage of the protrusion, the distal-end-directional-path elastically-deformable portion narrows the narrowed portion in distal-end-directional path so that it is possible to avoid entry of the protrusion into the initial position when the protrusion recedes after puncturing with the needle.

Furthermore, it is preferable that the outer cylinder includes one elastic member that composes the proximal-end-directional-path elastically-deformable portion and the distal-end-directional-path elastically-deformable portion, wherein the elastic member is disposed between the initial position and the lock position in a circumferential direction of the outer cylinder, and extends from a proximal end portion of the outer cylinder in the distal end direction.

In this manner, since one elastic member composes the proximal-end-directional-path elastically-deformable portion and the distal-end-directional-path elastically-deformable, the guiding path structure can be formed much easier, which facilitates the manufacture.

Alternatively, the outer cylinder may include: a first elastic member that is disposed in the vicinity of the lock position that composes the proximal-end-directional-path elastically-deformable portion; and a second elastic member that is disposed at a position different from the first elastic member in the peripheral wall of the outer cylinder and composes the distal-end-directional-path elastically-deformable portion.

In this manner, since the proximal-end-directional-path elastically-deformable portion is configured to include the first elastic member and the distal-end-directional-path elastically-deformable portion is configured to include the second elastic member, it is possible to separately design elastic force applied to the cam structure and to preferably guide and regulate the cam structure by the guiding path structure.

Furthermore, it is preferable that the regulating portion includes a guiding portion that is configured to guide the cam structure disposed in the lock position in a direction apart from the proximal-end-directional-path elastically-deformable portion when the outer cylinder moves in the proximal end direction with respect to the inner member while the cam structure is at the lock position.

Accordingly, even when force for re-exposing the needle is applied, the cam structure in contact with the guiding portion is guided in the direction apart from the proximal-end-directional-path elastically-deformable portion so that it is possible to reliably engage the cam structure and the regulating portion.

In order to achieve the aforementioned object, the medical device assembled body according to one embodiment further includes the protection device and the medical device to which the protection device is attached.

In this manner, the medical device assembled body is provided with the protection device attached to the medical device so that the user-friendliness enhances.

Furthermore, it is preferable that the medical device is a syringe that includes a barrel body having a space portion and a cap that is configured to seal the needle tip, the space portion being configured to store a liquid in a proximal end of the needle holder, and wherein a syringe is configured to discharge the liquid from the tip of the needle (16).

In this manner, the protection device is attached to the syringe so that the medical device assembled body can be provided as a highly safe product.

Still further, the medical device assembled body may be configured in such a manner that the inner member is rotatably disposed on an outer periphery of the barrel body, the outer cylinder extends from a position where at least a part of the needle is covered to a position where the inner member is covered, and the medical device assembled body (10, 10A to 10C) further comprises a cover that is configured to house the protection device and attach the protection device to the syringe.

In this manner, by covering the inner member and the outer cylinder with the cover, the protection device can be easily attached to the syringe. Furthermore, a user can use the protection device as if to handle the syringe. Still further, the protection device can be used with a commercially available syringe housed therein so that the versatility enhances.

The protection device and the medical device assembled body according to embodiments of the present application preferably prevent the re-exposure of the needle by smoothly moving the cam structure to the lock position after puncturing with the needle and by firmly preventing the cam structure guided to the lock position from being detached from the lock position.

BRIEF DESCRIPTION OF THE DRAWINGS

FIG. 6 is an illustrative drawing showing a first guiding path and a second guiding path virtually combined.

FIG. 7A is a first illustrative drawing of the first peripheral wall showing a movement of the first peripheral wall side of the medical device assembled body in FIG. 1; FIG. 7B is a first illustrative drawing of the second peripheral wall showing a movement of the second peripheral wall side of the medical device assembled body in FIG. 1; FIG. 7C is a second illustrative drawing of the first peripheral wall showing a movement following the movement in FIG. 7A; and FIG. 7D is a second illustrative drawing of the second peripheral wall showing a movement following the movement in FIG. 7B.

FIG. 8A is a third illustrative drawing of the first peripheral wall showing a movement following the movement in FIG. 7C; FIG. 8B is a third illustrative drawing of the second peripheral wall showing a movement following the movement in FIG. 7D; FIG. 8C is a fourth illustrative drawing of the first peripheral wall showing a movement following the movement in FIG. 8A; and FIG. 8D is a fourth illustrative drawing of the second peripheral wall showing a movement following the movement in FIG. 8B.

FIG. 9A is a fifth illustrative drawing of the first peripheral wall showing a movement following the movement in FIG. 8C; FIG. 9B is a fifth illustrative drawing of the second peripheral wall showing a movement following the movement in FIG. 8D; FIG. 9C is a sixth illustrative drawing of the first peripheral wall showing a movement following the movement in FIG. 9A; and FIG. 9D is a sixth illustrative drawing of the second peripheral wall showing a movement following the movement in FIG. 9B.

FIG. 10 is a perspective view showing an overall configuration of a medical device assembled body according to a second embodiment.

FIG. 12A is a first illustrative drawing of the first peripheral wall showing a movement of the first peripheral wall side of the medical device assembled body in FIG. 10; FIG.

12B is a first illustrative drawing of the second peripheral wall showing a movement of the second peripheral wall side of the medical device assembled body in FIG. 10; FIG. 12C is a second illustrative drawing of the first peripheral wall showing a movement following the movement in FIG. 12A; and FIG. 12D is a second illustrative drawing of the second peripheral wall showing a movement following the movement in FIG. 12B.

FIG. 13A is a third illustrative drawing of the first peripheral wall showing a movement following the movement in FIG. 12C; FIG. 13B is a third illustrative drawing of the second peripheral wall showing a movement following the movement in FIG. 12D; FIG. 13C is a fourth illustrative drawing of the first peripheral wall showing a movement following the movement in FIG. 13A; and FIG. 13D is a fourth illustrative drawing of the second peripheral wall showing a movement following the movement in FIG. 13B.

FIG. 14A is a fifth illustrative drawing of the first peripheral wall showing a movement following the movement in FIG. 13C; FIG. 14B is a fifth illustrative drawing of the second peripheral wall showing a movement following the movement in FIG. 13D; FIG. 14C is a sixth illustrative drawing of the first peripheral wall showing a movement following the movement in FIG. 14A; and FIG. 14D is a sixth illustrative drawing of the second peripheral wall showing a movement following the movement in FIG. 14B.

FIG. 16 is an exploded perspective view showing a protection device in FIG. 15.

FIG. 17A is a side view showing a state where a body is housed in an outer cylinder and a cover; and FIG. 17B is a side sectional view of the medical device assembled body in FIG. 17A.

FIG. 18A is a first illustrative drawing showing a movement of the medical device assembled body in FIG. 15; FIG. 18B is a second illustrative drawing showing a movement following the movement in FIG. 18A; and FIG. 18C is a third illustrative drawing showing a movement following the movement in FIG. 18B.

FIG. 19A is a first side view showing a relationship between an outer cylinder and an inner cylinder of a medical device assembled body according to a fourth embodiment; FIG. 19B is a second side view showing a relationship between the outer cylinder and the inner cylinder following the view in FIG. 19A; and FIG. 19C is a third side view showing a relationship between the outer cylinder and the inner cylinder following the view in FIG. 19B.

FIG. 20A is a fourth side view showing a relationship between the outer cylinder and the inner cylinder following the view in FIG. 19C; FIG. 20B is a fifth side view showing a relationship between the outer cylinder and the inner cylinder following the view in FIG. 20A; and FIG. 20C is a sixth side view showing a relationship between the outer cylinder and the inner cylinder following the view in FIG. 20B.

DETAILED DESCRIPTION

Embodiments of a protection device and a medical device assembled body will now be described in detail with reference to the accompanying drawings.

First Embodiment

Figure 1:
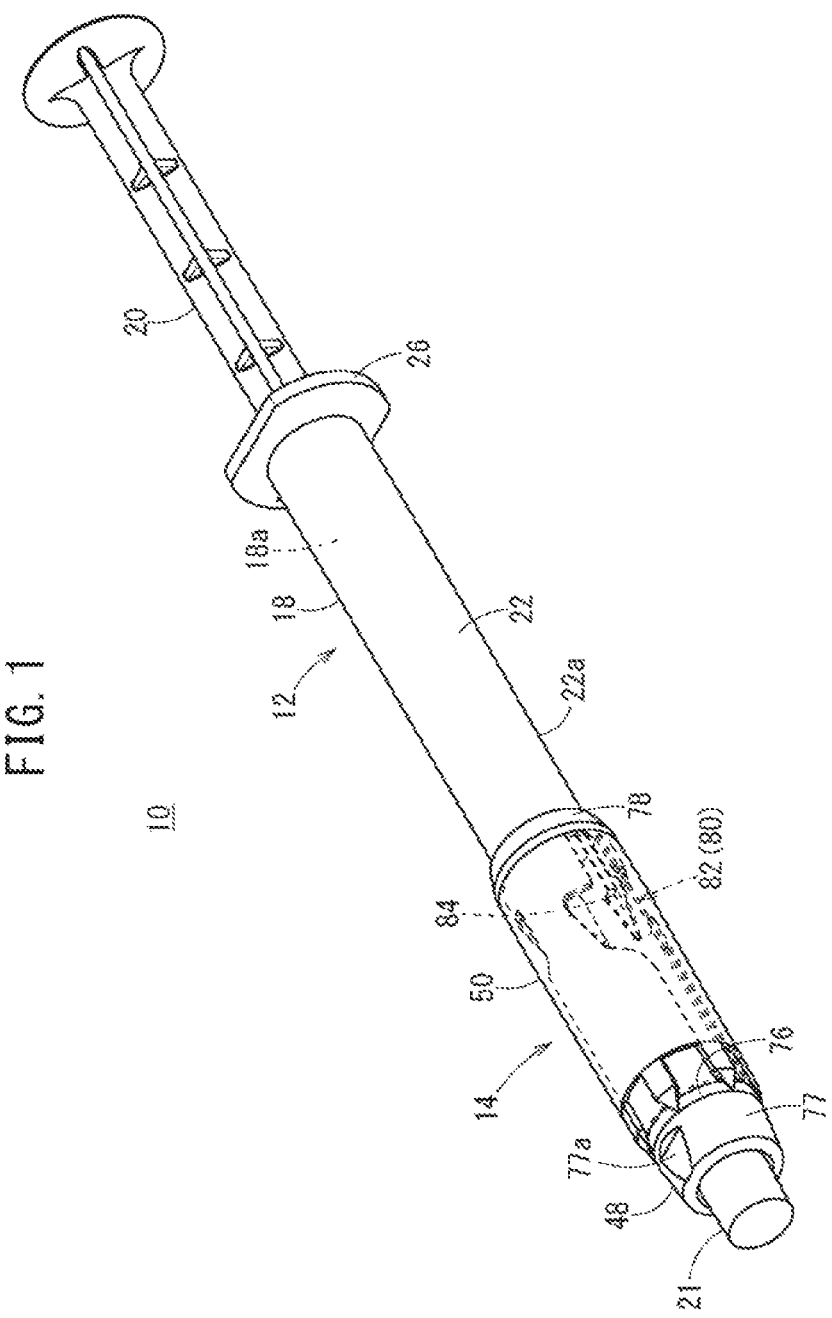
FIG. 1 is a perspective view showing an overall configuration of a medical device assembled body according to a first embodiment.

A medical device assembled body 10 according to a first embodiment is made as a pre-filled syringe pre-filled with a drug solution (liquid). As shown in FIG. 1, the medical device assembled body 10 is provided with a protection device 14 attached to a syringe 12 (medical device).

The protection device 14 is configured to improve safety and hygiene before using the syringe 12 and to prevent leakage of the drug solution. When using the medical device assembled body 10, a needle 16 of the syringe 12 (see FIG. 2) is exposed from a distal end under operation of a user (medical personnel or patient) so that a patient or a target of puncture can be punctured with the needle 16. After administration of the drug solution from the needle 16, the protection device 14 is pulled away from the patient and automatically re-houses the exposed needle 16, which enhances the safety after puncturing.

Figure 2:
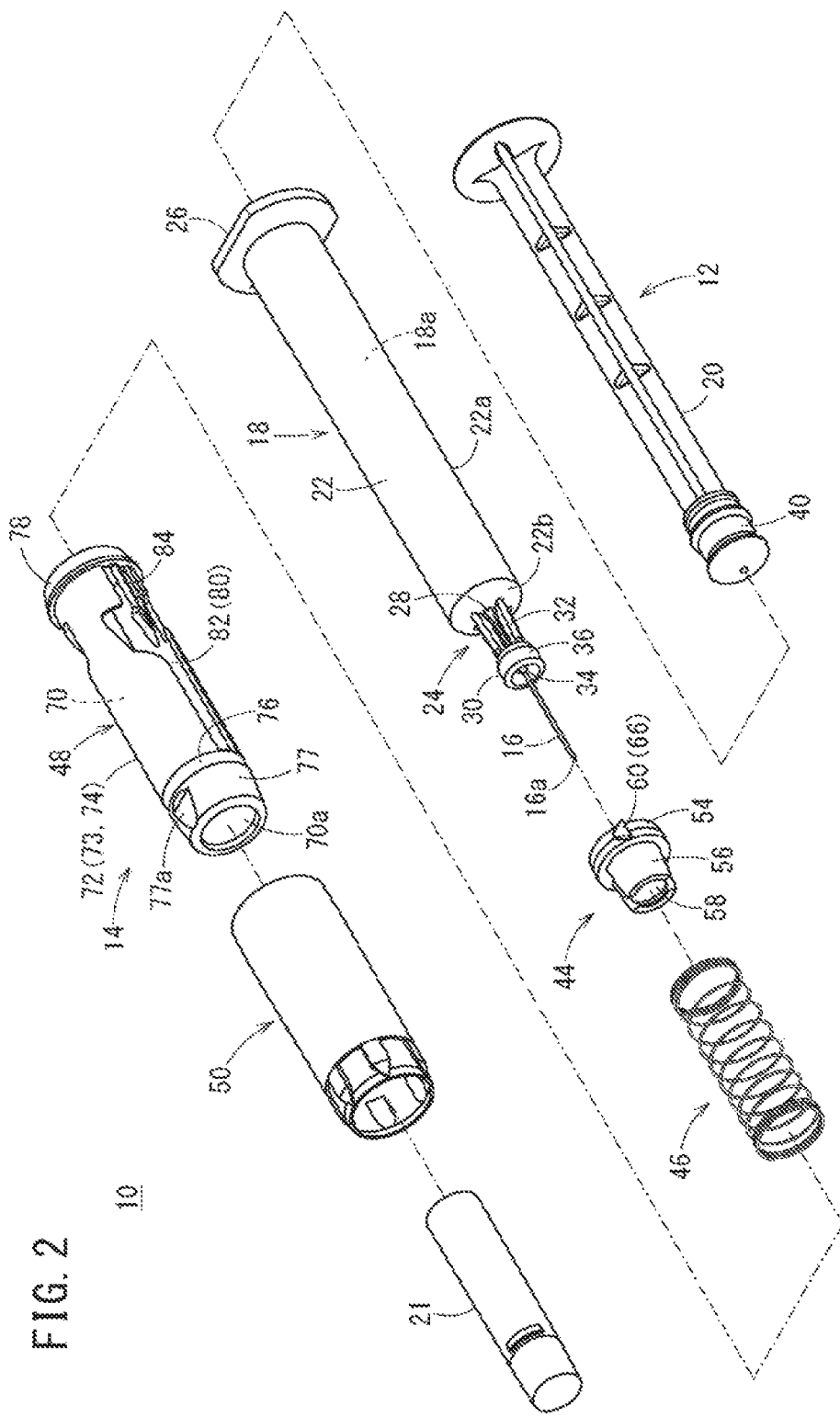
FIG. 2 is an exploded perspective view showing the medical device assembled body of FIG. 1.

As shown in FIG. 2, the syringe 12 attached with the protection device 14 includes the needle 16; a body 18 having a storage space 18a (space portion) in which the drug solution is stored; a gasket 40 inserted into the storage space 18a and slidable inside the body 18; and a plunger 20 for operating the gasket 40. The syringe 12 is also attached with a cap 21 to cover the needle 16.

The needle 16 is formed to have an appropriately small diameter, and a needle tip 16a thereof is sharpened. Inside the needle 16, a lead-out path 16b is provided to discharge the drug solution.

The body 18 includes a barrel body 22 having the storage space 18a inside; a needle holder 24 provided to a distal end of the barrel body 22; and a hook portion 26 provided to a proximal end of the barrel body 22. Each part is formed in an integrated manner at the time of manufacturing the body 18.

The barrel body 22 is formed in a cylindrical shape having a predetermined axial length and diameter in accordance with an amount of the drug solution stored in the storage space 18a. The barrel body 22 includes a cylindrical side wall 22a surrounding a peripheral side portion of the storage space 18a; and an end wall 22b linked to a distal end of the side wall 22a, protruded inward in a radial direction, and included in a bottom portion of the storage space 18a. The hook portion 26 is protruded outward from a periphery close to a proximal end of the side wall 22a and is configured in such a manner that a jig for holding the body 18 is hooked, for example, when filling the storage space 18a with the drug solution.

The needle holder 24 is connected to a distal end of the end wall 22b and is protruded in a distal end direction coaxially with the barrel body 22. It is preferable that an axial length of the needle holder 24 is formed shorter than an axial length of a part of the needle 16 protruded from the needle holder 24 toward the distal end. Accordingly, the medical device assembled body 10 can be downsized. The needle holder 24 holds the needle 16 with such a short dimension so that the needle holder 24 includes a supporting tubular portion 28 in a proximal end, and a bulging tubular portion 30 in a distal end.

Figure 3:
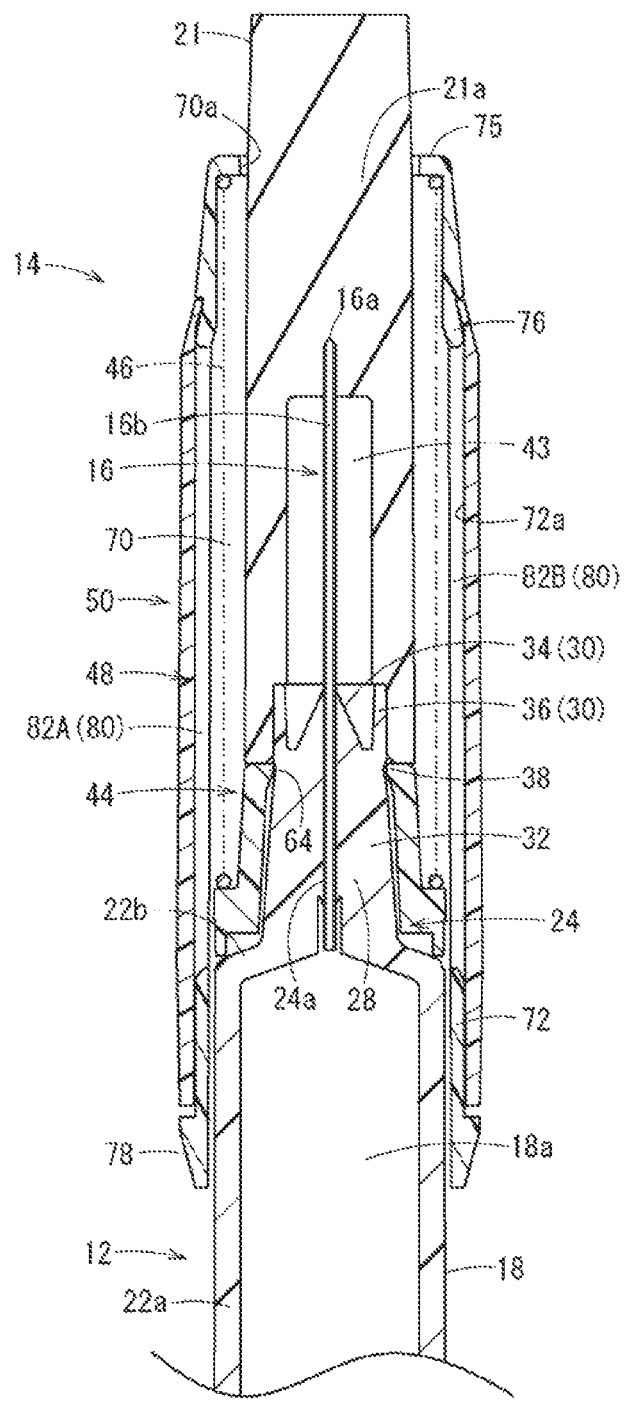
FIG. 3 is a cross sectional side view of a distal end of the medical device assembled body shown in FIG. 1.

The supporting tubular portion 28 protruded short from the end wall 22b fixes and holds the needle 16. Examples of a technique to fix the needle 16 include insert molding, thermal welding with high-frequency or laser, and adhesion with an adhesive. The supporting tubular portion 28 has a plurality (four) of reinforcing ribs 32 on its outer periphery in order to enhance the strength of the supporting tubular portion 28. Each reinforcing rib 32 extends from the end wall 22b to the bulging tubular portion 30. As shown in FIG. 3, a protrusive height of each reinforcing rib 32 gradually decreases in the distal end direction and becomes the lowest at a connecting part with the bulging tubular portion 30.

The bulging tubular portion 30 includes a central supporting portion 34 formed in a substantially conical shape for holding the needle 16; and an outer surrounding portion 36 circumferentially surrounding a side of the central supporting portion 34. A connecting part with each reinforcing rib 32 in a proximal end of the outer surrounding portion 36 tapers in a proximal end direction to forma constricted portion 38. This constricted portion 38 has a function to rotatably mount the inner cylinder 44 of the protection device 14. The constricted portion 38 is not limited to a tapered shape and may be simply formed, for example, as a step between the outer surrounding portion 36 and each reinforcing rib 32. Furthermore, the bulging tubular portion 30 and the supporting tubular portion 28 may be formed in a continuous cylindrical shape having a holding hole for holding the needle 16, and the constricted portion 38 may be formed between the bulging tubular portion 30 and the supporting tubular portion 28.

Referring back to FIG. 2, the plunger 20 of the syringe 12 serves as a pusher for the user to push out. A distal end portion of the plunger 20 is attached with the gasket 40 which is to be liquid-tightly inserted into the storage space 18a. Before being used, the medical device assembled body 10 as the pre-filled syringe may house only the gasket 40 in the body 18 without the plunger 20 being attached.

The cap 21 is formed, by a flexible resin material, in a tubular shape having a needle housing space 43 (see FIG. 3). The cap 21 is exposed from a distal end-opening 70a of the protection device 14 while covering the needle 16 until the medical device assembled body 10 is used. When using the medical device assembled body 10, the user pinches the exposed portion and pulls out in the distal end direction so that the cap 21 is removed. In the cap 21, a part closer to its distal end than the needle housing space 43 is formed into a relatively thick-walled portion 21a. This thick-walled portion 21a reliably closes the needle tip 16a of the needle 16 after puncturing.

When the cap 21 is attached to the needle holder 24, a proximal end of the cap 21 is brought into contact with the inner cylinder 44 of the protection device 14 so as to inhibit movement of the inner cylinder 44 before use, and is also brought into close contact with an outer periphery of the bulging tubular portion 30. Accordingly, the cap 21 keeps the entire needle 16 in an unexposed state before use of the syringe 12.

In regard to the protection device 14, it is attached so as to cover the needle 16, the needle holder 24, and the distal end of the barrel body 22. As shown in FIGS. 2 and 3, the protection device 14 includes the inner cylinder 44 (an inner member), a spring 46 (a biasing member), an outer cylinder 48, and a cover 50.

Figure 4A:
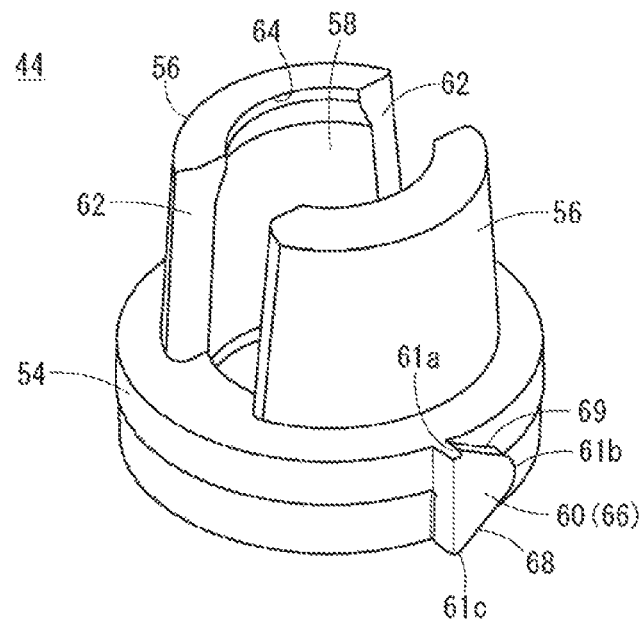
FIG. 4A is a perspective view showing an inner cylinder of a protection device.
Figure 4B:
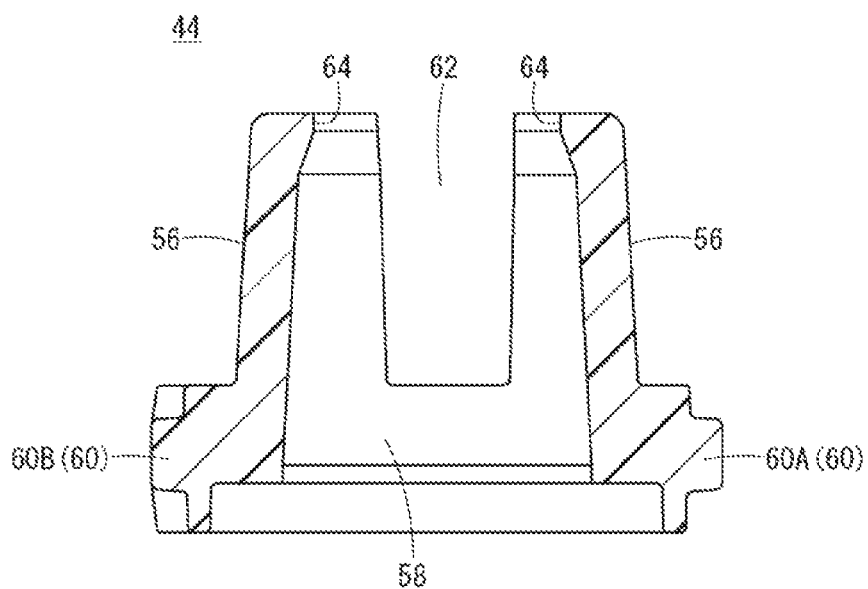
FIG. 4B is a cross sectional side view of the inner cylinder shown in FIG. 4A.

The inner cylinder 44 is rotatably mounted around the needle holder 24. The inner cylinder 44 includes an annular portion 54 circumferentially provided to a proximal end portion thereof; and a pair of projecting walls 56 projecting from a distal end surface of the annular portion 54. As shown in FIGS. 4A and 4B, an attachment hole 58 where the needle holder 24 is inserted and mounted is provided inside the annular portion 54 and the pair of projecting walls 56. In a side periphery of the annular portion 54, a pair of protrusions 60 is formed protruding outward in a radial direction. Furthermore, the distal end surface of the annular portion 54 is a base on which a proximal end of the spring 46 is disposed.

The annular portion 54 is formed to be relatively thick along an axial direction of the inner cylinder 44. An outer diameter of the annular portion 54 is set to be substantially equivalent to the outer diameter of the barrel body 22 when the inner cylinder 44 is attached to the needle holder 24. When attached to the needle holder 24, an inner diameter of the attachment hole 58 of the annular portion 54 is formed somewhat larger than an outer diameter of the supporting tubular portion 28, that is, a protrusive height of a pair of reinforcing ribs 32, so as to reduce frictional force due to contact between the supporting tubular portion 28.

The projecting walls 56 are linked to the inside (a part closer to the attachment hole 58) of the distal end surface of the annular portion 54. The pair of projecting walls 56 is provided to opposed positions, and a pair of split gaps 62, 62 communicating with the attachment hole 58 is formed between the pair of projecting walls 56. When the inner cylinder 44 is mounted on the needle holder 24, the pair of split gaps 62 elastically separates distal ends of the pair of projecting walls 56 from each other. Accordingly, the inner cylinder 44 can be easily attached to the needle holder 24.

Inner surfaces of the annular portion 54 and the pair of projecting walls 56 included in the attachment hole 58 are formed in a tapered shape that gradually tapers in the distal end direction when seen from a cross section. A pair of hooks 64 protruded slightly inward in the radial direction is provided to the inner surfaces in the distal ends of the pair of projecting walls 56. When the inner cylinder 44 is attached, the hooks 64 are disposed in positions where an outer periphery of the constricted portion 38 of the needle holder 24 is covered, and the hooks 64 are hooked into a distal end portion of the constricted portion 38. This prevents the inner cylinder 44 from coming off the needle holder 24 in the distal end direction.

The pair of protrusions 60, 60 is formed on an outer periphery of the annular portion 54 in an integrated manner. Received by (inserted into) a guiding path structure 80 of the outer cylinder 48, the pair of protrusions 60, 60 is included in a cam structure 66 that moves the inner cylinder 44 and the outer cylinder 48. Each protrusion 60 is formed in a triangular shape having a vertex in a side opposite to a rotative direction of the inner cylinder 44 at the time of puncturing when seen from a side view. Specifically, each protrusion 60 has two base corner portions 61a, 61c disposed in a distal end and proximal end of the annular portion 54 in the axial direction and one vertex corner portion 61b in an intermediate part in the axial direction, deviated from the two base corner portions 61a, 61c in a circumferential direction. In each protrusion 60, a proximal end-inclined side 68 and a distal end-inclined side 69 which are inclined in the circumferential direction are formed by connecting the base corner portions 61a, 61c with the vertex corner portion 61b. Furthermore, the vertex corner portion 61b is subjected to R-chamfering.

Referring back to FIG. 1, the outer cylinder 48 of the protection device 14 is formed to have an outer diameter slightly larger than that of the barrel body 22 of the body 18. A hollow portion 70 is provided inside the outer cylinder 48. This hollow portion 70 houses the needle 16, a distal end of the body 18, the inner cylinder 44, and the spring 46. As shown in FIG. 3, the outer cylinder 48 includes a peripheral wall 72 having a cylindrical shape; and an upper base wall 75 linked to a distal end of the peripheral wall 72 and slightly protruded inward in a radial direction.

The peripheral wall 72 surrounds a peripheral side portion of the hollow portion 70, and its axial length is formed to be longer than the entire length of the needle 16. An inner diameter of the peripheral wall 72 is set to be somewhat larger than the outer diameter of the barrel body 22 so as to smooth the relative movement of the outer cylinder 48 and to miniaturize the protection device 14. The upper base wall 75 is formed in a ring shape at the distal end of the peripheral wall 72, and a proximal end surface of the upper base wall 75 is a base on which a distal end of the spring 46 is disposed. In a distal end of the outer cylinder 48, the distal end-opening 70a is formed by an inner periphery of the upper base wall 75. The distal end-opening 70a communicates with the hollow portion 70 and exposes the needle 16 at the time of puncturing.

As shown in FIGS. 1 and 2, to prevent the cover 50 from being detached in the distal end direction, an annular recess 76 is provided in the circumferential direction in a part closer to the distal end of the peripheral wall 72. A part much closer to the distal end of the peripheral wall 72 than the annular recess 76 is a distal end-tapered portion 77 that is slightly tapered in the distal end direction so that the cap 21 can be easily held at the time of puncturing with the needle 16. A pair of flat surfaces 77a is formed on an outer periphery of the distal end-tapered portion 77. When the inner cylinder 44 is inserted into the outer cylinder 48, the flat surfaces 77a are used to match phases of the protrusions 60 of the inner cylinder 44 with guiding grooves (aftermentioned first and second guiding grooves 89, 102) that guide the protrusions 60 to initial positions in the outer cylinder 48. Furthermore, as shown in FIG. 3, a gap 72a is slightly provided between the cover 50 and the peripheral wall 72 so as to prevent contact between the cover 50 and an elastic member 84 of the outer cylinder 48. Still further, in a proximal end of the peripheral wall 72, a flanged portion 78 is formed, protruded outward in the radial direction. The flanged portion 78 reinforces a proximal end portion of the outer cylinder 48 and inhibit the detachment of the cover 50 in the proximal end direction.

Figure 5A:
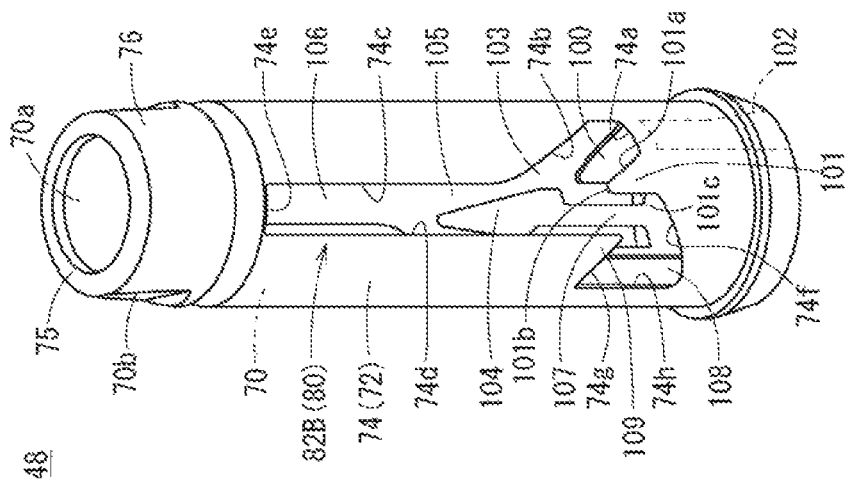
FIG. 5A is a perspective view showing a first peripheral wall of an outer cylinder.
Figure 5B:
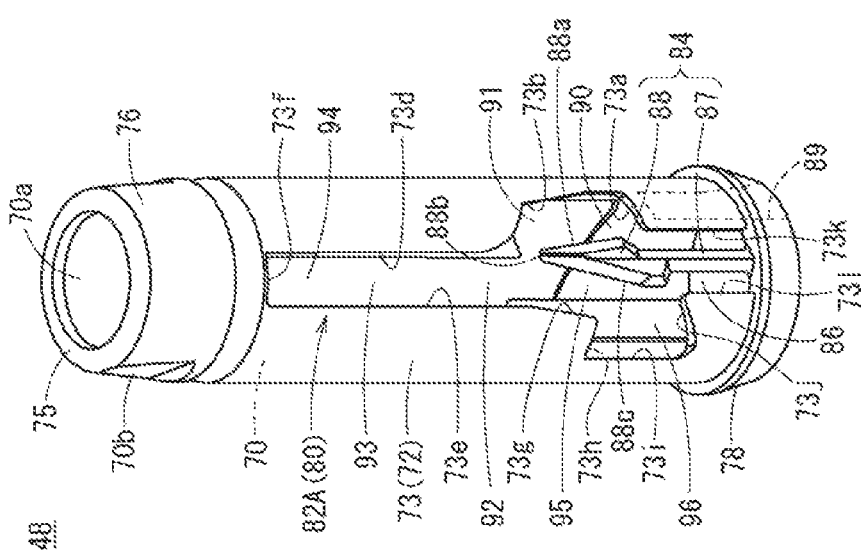
FIG. 5B is a perspective view showing a second peripheral wall of the outer cylinder.

Still further, the guiding path structure 80 for guiding the cam structure 66 (the pair of protrusions 60) of the inner cylinder 44 is formed between the vicinity of the proximal end of the peripheral wall 72 and the annular recess 76. As shown in FIGS. 5A and 5B, the guiding path structure 80 includes two guiding paths 82 provided at opposed positions across the hollow portion 70.

For the purpose of illustration, the guiding path 82 shown in the front of FIG. 5A is referred to as a first guiding path 82A, accordingly, the peripheral wall 72 having the first guiding path 82A of the outer cylinder 48 is also referred to as a first peripheral wall 73. Conversely, the guiding path 82 shown in the front of FIG. 5B is referred to as a second guiding path 82B, accordingly, the peripheral wall 72 having the second guiding path 82B is also referred to as a second peripheral wall 74.

The first and second guiding paths 82A, 82B allow the hollow portion 70 to communicate with the outside of the outer cylinder 48. A length of the first and second guiding paths 82A, 82B along the axial direction of the outer cylinder 48 is formed to be longer than an axial length of the inner cylinder 44. The first and second guiding paths 82A, 82B are formed in different shapes so as to apply different actions to the cam structure 66 of the inner cylinder 44.

Specifically, the first guiding path 82A is formed in a predetermined shape by inner edges of the first peripheral wall 73 formed by cutting out a part of the first peripheral wall 73. Inside the first guiding path 82A, there is provided the elastic member 84 supported by the proximal end portion of the outer cylinder 48. An extension space 86 for allowing the elastic member 84 to extend from the proximal end portion of the outer cylinder 48 is continuously provided to a part closer to a proximal end of the first guiding path 82A.

The elastic member 84 includes a rod-like elastically-deformable portion 87 that is protruded in the distal end direction in a circumferential center portion of the extension space 86; and a tilting portion 88 formed in a distal end of the elastically-deformable portion 87, having a shape of an arrow when seen from a planar view. The tilting portion 88 is disposed at a substantially central position of a relatively large space of the first guiding path 82A linked to a distal end of the extension space 86. The elastic member 84 is elastically deformable due to elastic force of the elastically-deformable portion 87 and tilts the tilting portion 88 inside the first guiding path 82A according to contact with the cam structure 66. Hereinafter, the protrusion 60 of the cam structure 66 disposed in the first guiding path 82A is also referred to as a first protrusion 60A.

The first guiding path 82A has a first initial position 90, a space allowing the first protrusion 60A to stand by before puncturing, at a position apart from the tilting portion 88 by a predetermined interval in the proximal end direction, with a phase shifting in the circumferential direction. In a state where the first protrusion 60A stands by at the first initial position 90, the contact between the first protrusion 60A and the elastic member 84 is prevented so as not to affect the elastic force of the elastic member 84. The first initial position 90 is set, by an inner edge 73a forming a proximal end thereof, at a position apart from the proximal end portion of the outer cylinder 48 by a predetermined interval in the distal end direction. Accordingly, in the state where the first protrusion 60A stands by at the first initial position 90, the proximal end portion of the outer cylinder 48 overlaps a distal end portion of the barrel body 22 so as to prevent backlash of the outer cylinder 48. As the inner edge 73a is caught in the first protrusion 60A, the outer cylinder 48 is prevented from dropping off the inner cylinder 44.

In an inner surface of the first peripheral wall 73, there is provided the first guiding groove 89 for introducing the first protrusion 60A to the first initial position 90 when the inner cylinder 44 is inserted into the outer cylinder 48. The first guiding groove 89 extends from the proximal end of the outer cylinder 48 to the vicinity of the inner edge 73a. The first guiding groove 89 tapers in the circumferential direction from the proximal end to a halfway position in the axial direction so that the first protrusion 60A can be easily guided to the first initial position 90 at the time of attachment. When attached, the first protrusion 60A passes over the first peripheral wall 73 adjacent to a proximal end of the inner edge 73a from the first guiding groove 89 so as to be disposed in the first guiding path 82A.

The first guiding path 82A has a first initial path 91 extending leftward (circumferential direction) and in the distal end direction in an inclined manner from the first initial position 90. The first initial path 91 is formed by a one-edge portion 88a on the right (a side closer to the first initial position 90) of the tilting portion 88 and an inner edge 73b of the first peripheral wall 73. The inner edge 73b is formed in a curved shape, curving inward from a halfway position closer to its distal end. An interval between the tilting portion 88 and the inner edge 73b is set to such a dimension that the tilting portion 88 does not come into contact with the inner edge 73b when the tilting portion 88 is inclined to the right (the side closer to the first initial position 90) due to the contact of the first protrusion 60A.

In a part of the first guiding path 82A slightly closer to the proximal end than the intermediate part in the axial direction, there is provided a first junction position 92 where the first initial path 91 joins a first intermediate path 93 and a first final path 95, which are to be described later. The first junction position 92 is positioned at a part closer to the distal end than a distal end-vertex 88b of the tilting portion 88. When the first protrusion 60A moves from the initial position to the first junction position 92, the needle tip 16a of the needle 16 comes close to the distal end-opening 70a of the outer cylinder 48. Therefore, when the needle tip 16a is accidentally exposed from the distal end-opening 70a of the outer cylinder 48, the first protrusion 60A moves to the after-mentioned lock position and the needle 16 cannot be reused.

Furthermore, the first intermediate path 93 of the first guiding path 82A linearly extends from the first junction position 92 in the distal end direction. The first intermediate path 93 is formed by a pair of inner edges 73d, 73e of the first peripheral wall 73, having a first puncture position 94 at a distal end of the first intermediate path 93 where the first protrusion 60A is guided at the time of puncturing with the needle 16. The first puncture position 94 is defined by an inner edge 73f of the first peripheral wall 73.

Still further, the first final path 95 of the first guiding path 82A extends leftward (circumferential direction) and in the proximal end direction in an inclined manner from the first junction position 92. The first final path 95 is formed by a one-edge portion 88c on the left (a side closer to a first lock position 96) of the tilting portion 88 and an inner edge 73g of the first peripheral wall 73. An interval between the one-edge portion 88c and the inner edge 73g of the tilting portion 88 is set to such a dimension that the tilting portion 88 does not come into contact with the inner edge 73g when the tilting portion 88 is inclined to the left (the side closer to the first lock position 96) due to the contact of the first protrusion 60A.

A part closer to an inclined proximal end of the first final path 95 is a first lock position 96, a space where the first protrusion 60A after puncturing is guided. The first lock position 96 is provided to a part slightly closer to the proximal end than the first initial position 90. The first lock position 96 includes an inner edge 73h of the first peripheral wall 73 linked to the inner edge 73g and parallel to the circumferential direction; an inner edge 73i of the first peripheral wall 73 linked to the inner edge 73h and parallel to the axial direction; and an inner edge 73j of the first peripheral wall 73 linked to the inner edge 73i and formed in a curved shape that is slightly recessed in the proximal end direction. The inner edge 73j extends to the vicinity of the tilting portion 88, serving as a rotation-inducing portion in a proximal-end-directional path that rotates the inner cylinder 44 together with the elastic member 84. The inner edge 73j is linked to inner edges 73k, 73l included in the extension space 86.

The second guiding path 82B of the guiding path structure 80 will now be described with reference to FIG. 5B. Hereinafter, the protrusion 60 disposed in the second guiding path 82B and in the opposite side of the first protrusion 60A is also referred to as a second protrusion 60B. The second guiding path 82B is formed in a predetermined shape by inner edges of the second peripheral wall 74 formed by cutting out a part of the second peripheral wall 74. The second guiding path 82B is formed in a shape similar to the first guiding path 82A, but the elastic member 84 is not provided thereto, and shapes of some inner edges of the second peripheral wall 74 are different.

The second guiding path 82B has a second initial position 100, a space for allowing the second protrusion 60B before puncturing to stand by. The second initial position 100 is set, by an inner edge 74a of the second peripheral wall 74, at a position apart from the proximal end portion of the outer cylinder 48 by a predetermined interval. Accordingly, in a state where the second protrusion 60B stands by at the second initial position 100, the proximal end portion of the outer cylinder 48 overlaps the distal end portion of the barrel body 22 so as to prevent backlash of the outer cylinder 48. As the inner edge 74a is caught in the second protrusion 60B, the outer cylinder 48 is prevented from dropping off the inner cylinder 44.

Furthermore, a sectioning projection 101 that separates the second initial position 100 from the after-mentioned second final path 107 stretches on the left of the inner edge 74a of the second guiding path 82B. Still further, in an inner surface of the second peripheral wall 74, there is provided the second guiding groove 102 for introducing the second protrusion 60B to the second initial position 100 when the protection device 14 is attached. The second guiding groove 102 is at a position opposing the first guiding groove 89 and extends from the proximal end of the outer cylinder 48 to the vicinity of the inner edge 74a. This second guiding groove 102 also tapers in the circumferential direction from the proximal end to a halfway position in the axial direction so that the second protrusion 60B can be easily guided to the second initial position 100 when the inner cylinder 44 is inserted into the outer cylinder 48.

The second guiding path 82B has a second initial path 103 extending leftward (circumferential direction) and in the distal end direction in an inclined manner from the second initial position 100. The second initial path 103 is formed in such a manner that an edge (an inner edge 101a of the second peripheral wall 74) in a side closer to the second initial position 100 of the sectioning projection 101 and an inner edge 74b of the second peripheral wall 74 opposing to the inner edge 101a are in parallel with each other, extending at the same inclination angle. The inner edge 74b extends longer than the inner edge 101a toward the distal end.

The second initial path 103 is linked to a second junction position 104 formed in a relatively wide space in a part closer to the distal end than a distal end-vertex 101b of the sectioning projection 101. The second guiding path 82B has a second intermediate path 105 extending linearly from the second junction position 104 in the distal end direction. The second intermediate path 105 is formed by a pair of inner edges 74c, 74d of the second peripheral wall 74, having a second puncture position 106 at a distal end of the second intermediate path 105 where the second protrusion 60B is guided at the time of puncturing with the needle 16. The second puncture position 106 is defined by an inner edge 74e of the second peripheral wall 74.

The second guiding path 82B further has the second final path 107 extending linearly from the second junction position 104 in the proximal end direction. The second final path 107 includes an edge of the sectioning projection 101 (an inner edge 101c of the second peripheral wall 74) in a side closer to a second lock position 108; and a proximal end portion of the inner edge 74d extending linearly in the axial direction from the second puncture position 106. Furthermore, the second final path 107 guides the second protrusion 60B to the second lock position 108 as an inner edge 74f linked to the inner edge 101c of the sectioning projection 101 extends lengthwise and leftward (circumferential direction) and in the proximal end direction in an inclined manner.

In a side opposite to the sectioning projection 101 across the second final path 107, there is provided a guide 109 having an acute corner, curved leftward (circumferential direction) and in the distal end direction from a proximal end of the inner edge 74d of the second peripheral wall 74. An inner edge 74g of the second peripheral wall 74 included in the guide 109 extends with being inclined leftward (in a direction apart from the second final path 107) and in the distal end direction. The second lock position 108 includes the inner edge 74g of the guide 109; an inner edge 74h of the second peripheral wall 74 linked to the inner edge 74g, linearly extending in the axial direction; and the inner edge 74f of the second peripheral wall 74 linked to the inner edge 74h and the sectioning projection 101, formed in a curved shape that is slightly recessed in the proximal end direction. A distal end portion of the inner edge 74f serves as a rotation-inducing portion in a proximal-end-directional path that rotates the inner cylinder 44.

Cooperating with each other, the first and second guiding paths 82A, 82B guide the first protrusion 60A and the second protrusion 60B of the inner cylinder 44 to pass through appropriate paths at the time of puncturing with the needle 16. Specifically, as shown in FIG. 6, when the second guiding path 82B is virtually superimposed on the first guiding path 82A, the inner edges 74a to 74h, 101a, and 101c of the second peripheral wall 74 included in the second guiding path 82B are disposed in an inner side, compared to the inner edges 73a to 73l of the first peripheral wall 73 included in the first guiding path 82A indicated by the solid line. In FIG. 6, those portions are indicated by the dotted line.

In other words, the guiding path structure 80 has a distal-end-directional path 110 as a guiding path that guides the cam structure 66 (the first and second protrusions 60A, 60B) from the initial position (first and second initial positions 90, 100) to the puncture position (first and second positions for puncture 94, 106) at the time of puncturing. This distal-end-directional path 110 is formed by the first initial path 91, first junction position 92, first intermediate path 93, second initial path 103, second junction position 104, and second intermediate path 105. The guiding path structure 80 also has a proximal-end-directional path 112 that guides the cam structure 66 (the first and second protrusions 60A, 60B) from the puncture position (the first and second positions for puncture 94, 106) to the lock position (the first and second lock positions 96, 108) after puncturing. The proximal-end-directional path 112 is formed by the first intermediate path 93, first junction position 92, first final path 95, second intermediate path 105, second junction position 104, and second final path 107.

In the middle region of the distal-end-directional path 110, there is provided a narrowed portion 110a (a distal-end-directional-path narrowed portion) having a width narrower than that of the first protrusion 60A in the distal-end-directional path 110 due to a relationship between the one-edge portion 88a of the elastic member 84 serving as an distal-end-directional-path elastically-deformable, and the inner edge 74b of the second peripheral wall 74 serving as an edge in the distal-end-directional path. Therefore, when the cam structure 66 passes through the narrowed portion 110a, the cam structure 66 guided by the inner edge 74b comes into contact with the elastic member 84, and the elastic member 84 elastically deforms to the left (the side closer to the first lock position 96), allowing the passage of the cam structure 66. After the passage of the cam structure 66, the elastic member 84 elastically reverts to the first state, restoring the width of the narrowed portion 110a to the original width. In other words, the elastic member 84 is the distal-end-directional-path elastically-deformable portion that changes the width of the distal-end-directional path 110.

When the cam structure 66 moves along the distal-end-directional path 110, the vertex corner portion 61b of the second protrusion 60B comes into contact with the inner edge 74b of the second initial path 103. Since the vertex corner portion 61b is subjected to R-chamfering, friction due to the contact with the inner edge 74b is reduced, which brings about smooth movement of the cam structure 66.

In the middle region of the proximal-end-directional path 112, there is provided a narrowed portion 112a (a narrowed portion in the proximal end-direction path) having a width narrower than that of the first protrusion 60A in the proximal-end-directional path 112 due to a relationship between the one-edge portion 88c of the elastic member 84 and the inner edge 74d of the second peripheral wall 74 serving as an edge in the proximal-end-directional path 112. Therefore, when the cam structure 66 passes through the narrowed portion 112a, the cam structure 66 guided by the inner edge 74d comes into contact with the elastic member 84, and the elastic member 84 elastically deforms to the right (the side closer to the first initial position 90), allowing the passage of the cam structure 66. After the passage of the cam structure 66, the elastic member 84 elastically reverts to the first state, restoring the width of the narrowed portion 112a to the original width. In other words, the elastic member 84 is the proximal-end-directional-path elastically-deformable portion that changes the width of the proximal-end-directional path 112. Note that it is preferable that only one proximal-end-directional-path elastically-deformable portion is formed in the outer cylinder. Accordingly, when the cam structure 66 moves from the first and second positions for puncture 94, 106 to the first and second lock positions 96, 108, only one portion elastically deforms by contacting with the cam structure 66 so that the cam structure 66 can easily pass through the narrowed portion 112a.

When the cam structure 66 moves along the proximal-end-directional path 112, the narrowed portion 110a is narrowed by the elastic member 84 so that the cam structure 66 is prevented from entering the first and second initial paths 91, 103. Furthermore, the R-chamfered vertex corner portion 61b of the first protrusion 60A comes into contact with the one-edge portion 88c of the tilting portion 88 so that friction due to the contact is reduced and the cam structure 66 is smoothly guided to the first and second lock positions 96, 108. Particularly, when the cam structure 66 moves to the first and second lock positions 96, 108, the inner edge 73j of the first guiding path 82A and the inner edge 74f of the second guiding path 82B come into contact with the cam structure 66 so as to easily rotate the inner cylinder 44 relative to the outer cylinder 48.

Returning to FIGS. 1 and 2, the cover 50 is attached to the peripheral wall 72 of the outer cylinder 48 so as to cover the guiding path structure 80. An axial length of the cover 50 is equivalent to a length from the flanged portion 78 of the outer cylinder 48 to the annular recess 76 so that the cover 50 can cover the entire guiding path structure 80. An outer diameter of the cover 50 is substantially equivalent to an outer diameter of the flanged portion 78. Inadvertent contact with respect to the cam structure 66 and the guiding path structure 80 can be avoided by the cover 50, which enhances the safety of the protection device 14.

As shown in FIGS. 2 and 3, the proximal end of the spring 46 of the protection device 14 is in contact with the distal end surface of the annular portion 54 of the inner cylinder 44. The distal end of the spring 46 is in contact with the proximal end surface of the upper base wall 75 provided inside the outer cylinder 48. The spring 46 elastically contracts as the outer cylinder 48 moves relative to the inner cylinder 44 in the proximal end direction under an operation of the user according to the puncture with the needle 16.

Elastic reversion of the spring 46 after puncturing imparts the outer cylinder 48 with biasing force so that the outer cylinder 48 moves relative to the inner cylinder 44 in the distal end direction. Furthermore, the spring 46 is a coil spring wound toward the proximal end, oriented in a direction equivalent to the rotative direction of the inner cylinder 44 with respect to the outer cylinder 48 when the cam structure 66 moves from the first and second initial positions 90, 100 to the first and second lock positions 96, 108. Accordingly, when the cam structure 66 moves from the first and second positions for puncture 94, 106 to the first and second lock positions 96, 108, the proximal end of the spring 46 interferes with the inner cylinder 44 so as to prevent defective rotation of the inner cylinder 44.

The medical device assembled body 10 according to the present embodiment is basically configured as described above, and its function effect will now be described specifically.

As described above, the medical device assembled body 10 is provided with the storage space 18a storing the drug solution and sealed with the gasket 40. As shown in FIGS. 7A and 7B, the medical device assembled body 10 prevents exposure of the needle 16 (see FIG. 2) and leakage of the drug solution by the cap 21 inserted into the outer cylinder 48. When using the medical device assembled body 10, the user attaches the plunger 20 to the gasket 40, pinches the cap 21 and pulls it out in the distal end direction. Accordingly, the medical device assembled body 10 is set to a state before puncturing, ready for puncturing the patient and administering the drug solution. In the state before puncturing, the cam structure 66 (first and second protrusions 60A, 60B) of the inner cylinder 44 is positioned at the initial position (first and second initial positions 90, 100) of the guiding path structure 80 of the outer cylinder 48.

At the time of puncturing with the needle 16, the user simply fixes the distal end-tapered portion 77 of the outer cylinder 48 to a punctured part (arm or the like) of the patient, and advances the syringe 12 with respect to the outer cylinder 48. Accordingly, as shown in FIGS. 7C and 7D, the needle 16, body 18, and inner cylinder 44 displace in the distal end direction with respect to the outer cylinder 48 and the cover 50. Thus, the needle 16 is gradually exposed from the distal end-opening 70a of the outer cylinder 48. At this time, the spring 46 contracts in the axial direction.

Furthermore, as the syringe 12 advances, the cam structure 66 (the first and second protrusions 60A, 60B) of the inner cylinder 44 moves in the distal end direction from the first and second initial positions 90, 100, where the cam structure 66 has been standing by, through the distal-end-directional path 110 of the guiding path structure 80 (see also FIG. 6). The inner cylinder 44 rotatably attached to the needle holder 24 rotates in the circumferential direction as the cam structure 66 is guided to the distal-end-directional path 110.

When the cam structure 66 moves in the distal end direction in the distal-end-directional path 110, the second protrusion 60B is guided by the inner edge 74b (a distal-end-directional-path rotation-inducing portion) of the second initial path 103, and the first protrusion 60A moves toward the one-edge portion 88a of the elastic member 84. In the narrowed portion 110a, the first protrusion 60A contacts with the elastic member 84 and makes the elastic member 84 deform elastically to the left (the side closer to the first lock position 96) so as to pass therethrough. The elastic member 84 elastically reverts to the first state after the passage of the cam structure 66.

When passing through the narrowed portion 110a, the cam structure 66 (the first and second protrusions 60A, 60B) passes through the distal-end-directional path 110 (the first and second intermediate paths 93, 105) and proceeds to the first and second positions for puncture 94, 106. Accordingly, as shown in FIGS. 8A and 8B, the needle 16 is sufficiently exposed from the distal end-opening 70a of the outer cylinder 48 and the patient can be punctured with the needle 16. After puncturing with the needle 16, the user pushes out the plunger 20 to administer the drug solution stored in the storage space 18a.

After administration of the drug solution, the user withdraws the syringe 12 from the patient in order to pull out the needle 16 from the patient. At this time, the outer cylinder 48 and the cover 50 are biased by the spring 46 contracted inside the hollow portion 70, and as shown in FIGS. 8C and 8D, the outer cylinder 48 and the cover 50 move in the distal end direction relative to the needle 16, inner cylinder 44, and body 18. With this movement, the cam structure 66 recedes with respect to the guiding path structure 80.

The cam structure 66 (the first and second protrusions 60A, 60B) passes from the first and second positions for puncture 94, 106 to the first and second lock positions 96, 108 through the proximal-end-directional path 112 of the outer cylinder 48. The cam structure 66 moves along the proximal-end-directional path 112 formed substantially linearly by the first guiding path 82A and the second guiding path 82B. The cam structure 66 recedes inside the guiding path structure 80 with weak frictional force while hardly rotating the inner cylinder 44.

In the narrowed portion 112a, the second protrusion 60B is guided by the inner edge 74d of the second final path 107, and the first protrusion 60A comes into contact with the one-edge portion 88c of the elastic member 84, which makes the elastic member 84 deform elastically to the right (the side closer to the first initial position 90). At this time, the vertex corner portion 61b of the first protrusion 60A is guided by the one-edge portion 88c of the elastic member 84 to the left (the side closer to the first lock position 96). Furthermore, when passing through the proximal-end-directional path 112, the cam structure 66 is prevented from entering the distal-end-directional path 110 since the narrowed portion 110a of the distal-end-directional path 110 is narrower than the width of the first protrusion 60A in the proximal-end-directional path 112.

The cam structure 66 having passed through the narrowed portion 112a rotates the inner cylinder 44 in the circumferential direction in accordance with to the inner edge 73j of the first guiding path 82A, the one-edge portion 88c of the elastic member 84, and the inner edge 74f of the second guiding path 82B, and then moves to the first and second lock positions 96, 108 as shown in FIGS. 9A and 9B. When the cam structure 66 moves to the first and second lock positions 96, 108, the needle 16, body 18, and inner cylinder 44 stop moving relative to the outer cylinder 48, thereby the needle 16 is housed inside the outer cylinder 48.

The protection device 14 can prevent re-advancement (re-exposure) of the needle 16 when the cam structure 66 moves to the first and second lock positions 96, 108. In other words, as shown in FIGS. 9C and 9D, the inner edge 74g of the guide 109 opposes a distal end of the cam structure 66. Therefore, even when the needle 16 and the inner cylinder 44 advances relative to the outer cylinder 48 in the distal end direction, the cam structure 66 is caught in the inner edge 74g. In this manner, the inner edge 74g serves as a regulating portion that inhibits the movement of the cam structure 66 in the distal end direction with respect to the outer cylinder 48. Furthermore, since the inner edge 74g is inclined in the distal end direction and in a direction apart from the second final path 107, the second protrusion 60B is positively moved away from the second final path 107. In other words, since the inner edge 74g serves as a guiding portion that guides the cam structure 66 disposed in the lock position in a direction apart from the proximal-end-directional-path elastically-deformable portion when the outer cylinder 48 moves in the proximal end direction relative to the inner cylinder 44 while the cam structure 66 is in the lock position, the engagement between the cam structure 66 and the inner edge 74g or the regulating portion becomes much stronger. As shown in FIG. 6, the inner edge 73h of the first peripheral wall 73 also opposes the distal end of the cam structure 66. Therefore, when the needle 16 and the inner cylinder 44 advance linearly in the distal end direction relative to the outer cylinder 48, the cam structure 66 is also caught in the inner edge 73h. In other words, the inner edge 73h can also serve as a regulating portion for regulating the movement of the cam structure 66 in the distal end direction with respect to the outer cylinder 48.

Furthermore, the elastic member 84 is disposed on the right (a side closer to the proximal-end-directional path 112) of the first and second lock positions 96, 108 so that the narrowed portion 112a is made narrower than the width of the first protrusion 60A in the proximal-end-directional path 112, which prevents the cam structure 66 from entering the narrowed portion 112a. In particular, even when the inner cylinder 44 rotates around an axis with respect to the outer cylinder 48 and the cam structure 66 comes into contact with the elastic member 84, the elastic member 84 elastically pushes back the protrusion 60 so as to inhibit the rotation of the inner cylinder 44 with respect to the outer cylinder 48. Therefore, the elastic member 84 prevents the engagement between the cam structure 66 and the inner edge 74g from being loosened and preferably inhibits the re-exposure of the needle 16.

As described above, in the medical device assembled body 10 and the protection device 14 according to the present embodiment, the guiding path structure 80 of the outer cylinder 48 includes, at different positions, the proximal-end-directional-path elastically-deformable portion (elastic member 84) that prevents the cam structure 66 from moving from the lock position to the puncture position; and the regulating portions (inner edge 74g, inner edge 73h) that prevent the cam structure 66 disposed in the lock position from moving in the distal end direction. In other words, the inner edge 74g and the inner edge 73h or the regulating portions are formed separately from the elastic member 84 or the proximal-end-directional-path elastically-deformable portion so as to enhance the rigidity and to firmly prevent the cam structure 66 from being detached from the first and second lock positions 96, 108 even when acting force is applied from the cam structure 66. Furthermore, the elastic member 84 or the proximal-end-directional-path elastically-deformable portion inhibits rotation of the inner cylinder 44 by contacting with the cam structure 66 so as to prevent the engagement of the cam structure 66 at the first and second lock positions 96, 108 from being loosened. Therefore, it is possible to preferably prevent the re-exposure of the needle 16 after puncturing with the needle 16.

In this case, the elastic member 84 elastically deforms by contacting with the first protrusion 60A so as to allow the first protrusion 60A to pass through the narrowed portion 112a substantially linearly along an axis of the outer cylinder 48, whereby restraining friction when the cam structure 66 moves along the proximal-end-directional path 112. Accordingly, the biasing force of the spring 46 is weakened, which facilitates the puncturing operation with the needle 16. Furthermore, as the proximal-end-directional path 112 makes the cam structure 66 move linearly, it is possible to further restrain the friction between the cam structure 66 and the proximal-end-directional path 112 and to weaken the biasing force of the spring 46. In addition, the guiding path structure 80 has the inner edge 74b so that it is possible to rotate the inner cylinder 44 at the time of puncturing and to prevent the cam structure 66 from returning to the first and second initial positions 90, 100.

Furthermore, the protection device 14 is provided with the elastic member 84, disposed in the first guiding path 82A, as the proximal-end-directional-path elastically-deformable portion, and is provided with the inner edge 74g, disposed in the second guiding path 82B, as the regulating portion that inhibits the movement of the cam structure 66 in the distal end direction with respect to the outer cylinder 48 so as to reliably prevent the cam structure 66 from being detached from the first and second lock positions 96, 108.

Still further, the elastic member 84 forms the gap of the narrowed portion 110a smaller than the width of the protrusion 60 in the distal-end-directional path 110 so that the protection device 14 makes the elastic member 84 elastically deform in such a manner that the protrusion 60 smoothly passes through the narrowed portion 110a when moving along the narrowed portion 110a. After the passage, the elastic member 84 narrows the narrowed portion 110a so that it is possible to reliably avoid the entry into the first and second initial positions 90, 100 after puncturing. Still further, in the protection device 14, one elastic member 84 is included in the distal-end-directional-path elastically-deformable portion and the proximal-end-directional-path elastically-deformable portion so that the guiding path structure 80 is further simplified, which facilitates the manufacture. Still further, the inner edge 74g or the regulating portion serves as the guiding portion that guides the cam structure 66 disposed in the lock position in the direction apart from the proximal-end-directional-path elastically-deformable portion when the force for re-exposing the needle 16 is applied so that the engagement between the cam structure 66 and the regulating portion becomes stronger.

It should be noted that the medical device assembled body 10 and the protection device 14 according to the present invention are not limited to the above embodiments and that various other embodiments are employable. For example, it is a matter of course that the number of protrusions 60 of the cam structure 66 and the number of guiding paths 82 of the guiding path structure 80 are not specifically restricted. Furthermore, the two protrusions 60 and the two guiding paths 82 are not limited to be provided to the opposed positions across a shaft center, but may be formed at any positions in the circumferential direction as long as the phases of the protrusions 60 and the guiding paths 82 are equivalent. Still further, the protection device 14 may have a configuration in which the cover 50 is omitted. Still further, the medical device assembled body 10 may be provided in a state where it is unfilled with the drug solution, that is, in a state where the protection device 14 is attached to the body 18 with the storage space 18a unfilled with the drug solution. In this case, after filling the storage space 18a with the drug solution, the gasket 40 is capped and the plunger 20 is attached as necessary, whereby manufacturing the medical device assembled body 10 pre-filled with the drug solution.

Second Embodiment

Hereinafter, a medical device assembled body 10A according to a second embodiment will be described with reference to FIGS. 10 to 14D. In the following description, it should be noted that the same reference numerals are given to components having the same configuration or the same functions as those of the medical device assembled body 10 according to the first embodiment, and a detailed description thereof will be omitted.

Figure 11A:
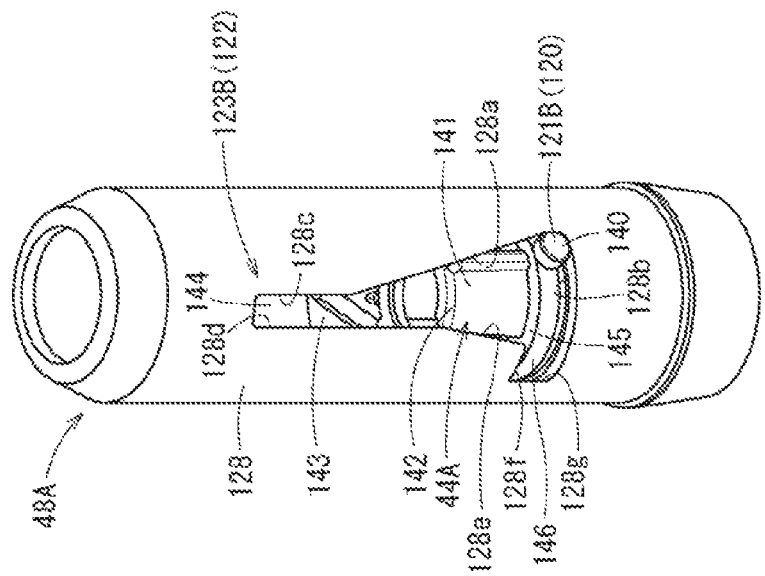
FIG. 11A is a perspective view showing a first peripheral wall of an outer cylinder shown in FIG. 10.
Figure 11B:
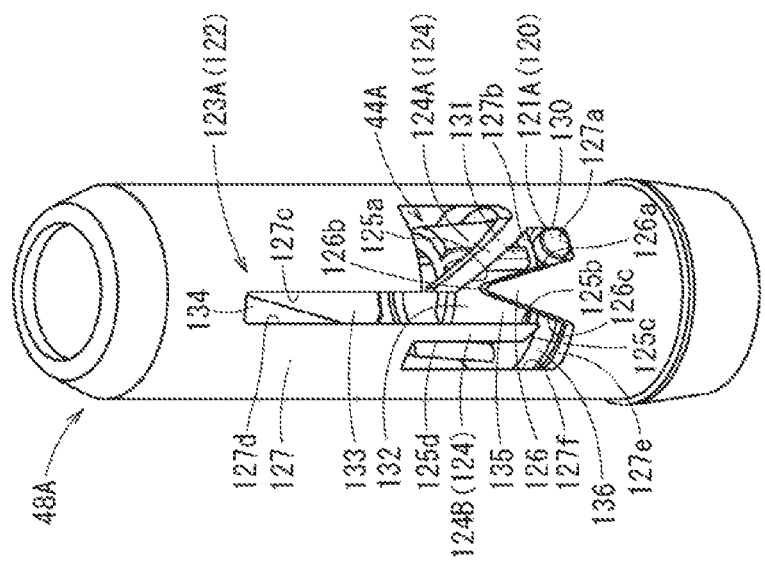
FIG. 11B is a perspective view showing a second peripheral wall of the outer cylinder shown in FIG. 10.
Figure 15:
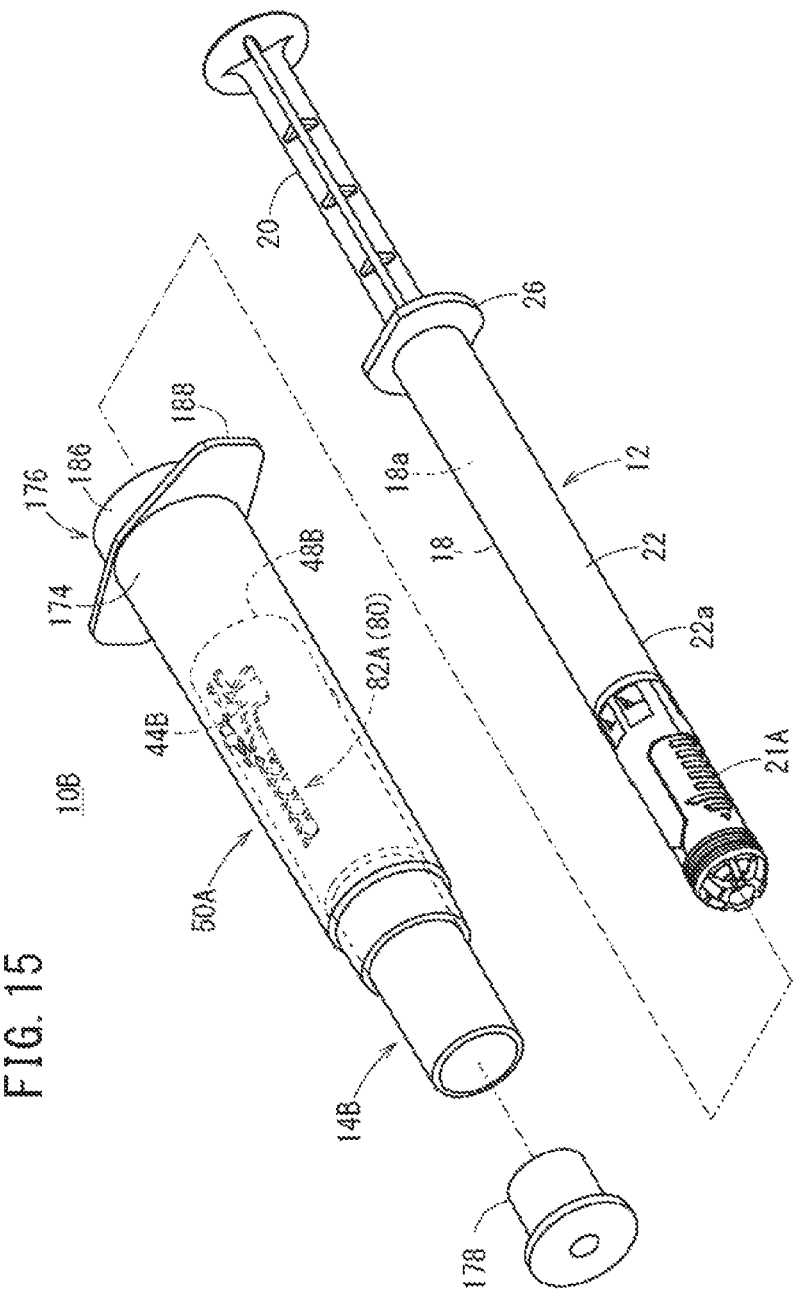
FIG. 15 is a partially exploded perspective view showing an entire configuration of a medical device assembled body according to a third embodiment.

As illustrated in FIGS. 10, 11A, and 11B, the medical device assembled body 10A according to the second embodiment differs from the medical device assembled body 10 according to the first embodiment in a cam structure 120 and a guiding path structure 122 of a protection device 14A. In an inner cylinder 44A of the protection device 14A, a pair of protrusions 121 (a first protrusion 121A, and a second protrusion 121B) having a cylindrical shape is protruded outward in a radial direction when seen from a side periphery. In short, the shapes of the cam structures 66, 120 are not specifically restricted, and various shapes may be employable unless the cam structures 66, 120 are movable in the guiding path structures 80, 122.

The guiding path structure 122 includes a pair of guiding paths 123 (a first guiding path 123A, and a second guiding path 123B) formed in an outer cylinder 48A. A first peripheral wall 127 included in the first guiding path 123A is provided with two elastic members 124 (a first elastic member 124A, and a second elastic member 124B) and a sectioning projection 126 having a triangular shape with a distal end-vertex 126b at its distal end. The second guiding path 123B is formed to have a shape substantially equivalent to that of the first guiding path 123A except that the elastic members 124 and the sectioning projection 126 having the triangular shape are not provided, and is formed to have an inner edge 128f of a second peripheral wall 128, serving as a regulating portion, in a distal end direction of a second lock position 146. A combination of the first and second guiding paths 123A, 123B forms a distal-end-directional path 150 and a proximal-end-directional path 152.

In the first guiding path 123A, a first initial position 130 where the first protrusion 121A is disposed before puncturing is formed by an inner edge 126a on the right of the sectioning projection 126 (in a side closer to the first initial position 130) and by an inner edge 127a and an inner edge 127b of the first peripheral wall 127. In a distal end of the first initial position 130, there is provided the first elastic member 124A inclined in the distal end direction and leftward (in a side closer to a first lock position 136). The first elastic member 124A is protruded with being inclined toward a proximal end further than the inner edge 126a of the sectioning projection 126. A first initial path 131 includes the inner edge 126a, and a one-edge portion 125a in a side of the first elastic member 124A closer to the first initial path 131. The first initial path 131 extends linearly from the first initial position 130 to a first junction position 132 disposed in the distal end direction of the sectioning projection 126 and leftward (in the side closer to the first lock position 136).

Between the one-edge portion 125a of the first elastic member 124A and the inner edge 126a near the distal end-vertex 126b of the sectioning projection 126, a gap is formed, having a width smaller than that of the protrusion 121 in the first initial path 131. In other words, in the middle region of the distal-end-directional path 150, a narrowed portion 150a or a distal-end-directional-path narrowed portion having a width narrower than that of the first protrusion 121A in the distal-end-directional path 150 is formed between the first elastic member 124A or a distal-end-directional-path elastically-deformable portion and the inner edge 126a or an edge of the distal-end-directional path 150. In the opposite side of the first guiding path 123A across the first elastic member 124A, a wide space is formed so as to allow the first elastic member 124A to deform elastically.

A first intermediate path 133 includes a pair of inner edges 127c, 127d of the first peripheral wall 127 and a one-edge portion 125b of the second elastic member 124B in a side closer to the first intermediate path 133. The first intermediate path 133 extends linearly from the first junction position 132 to a first puncture position 134. The second elastic member 124B is formed like a cantilever linearly extending in a proximal end direction from a halfway position of the first intermediate path 133. A proximal end surface of a proximal end portion 125c of the second elastic member 124B is formed in an inclined shape, cut in the distal end direction and rightward. A one-edge portion 125d in the opposite side of the one-edge portion 125b extends in the distal end direction from the proximal end portion 125c in parallel with the one-edge portion 125b.

A first final path 135 is disposed at a position closer to the proximal end than the first junction position 132, formed by an inner edge 126c on the left (the side closer to the first lock position 136) of the sectioning projection 126 and by the one-edge portion 125b of the second elastic member 124B, and communicating with the first lock position 136 in the side closer to the proximal end. The first final path 135 is provided with a gap, having a width smaller than that of the protrusion 121, between the proximal end portion 125c and the inner edge 126c as the second elastic member 124B extends linearly with respect to the inner edge 126c inclined in the side closer to the first lock position 136. In other words, in the middle region of the proximal-end-directional path 152, a narrowed portion 152a or a proximal-end-directional-path narrowed portion having a width narrower than that of the first protrusion 121A in the proximal-end-directional path 152 is formed between the second elastic member 124B or a proximal-end-directional-path elastically-deformable portion and the inner edge 126c or an edge in the proximal-end-directional path 152. Furthermore, a proximal end portion of the inner edge 126c of the sectioning projection 126 serves as a proximal-end-directional-path rotation-inducing portion configured to rotate the cam structure 120 that has passed through the narrowed portion 152a and to guide the first protrusion 121A to the first lock position 136.

The first lock position 136 is formed by the proximal end portion of the inner edge 126c of the sectioning projection 126 and by an inner edge 127e and an inner edge 127f of the first peripheral wall 127. A space having a length in an axial direction is formed in a part of the first lock position 136 closer to the distal end so as to allow the second elastic member 124B to deform elastically.

On the other hand, the second guiding path 123B is formed in a relatively wide and substantially triangular space. A second initial position 140 is set at a corner of the second guiding path 123B disposed in the proximal end direction and rightward. This corner is formed by an inner edge 128a of the second peripheral wall 128 inclined in the distal end direction and leftward and by an inner edge 128b extending in a circumferential direction.

A second initial path 141, a second junction position 142, and a second final path 145 are basically disposed at opposed positions of the first initial path 131, first junction position 132, and first final path 135, but they communicate with each other since the second guiding path 123B is formed in the wide space. The second intermediate path 143 includes a pair of inner edges 128c, 128d of the second peripheral wall 128 extending linearly in the axial direction. A second puncture position 144 is formed at a distal end portion of the second intermediate path 143. An inner edge 128e slightly inclined toward a side closer to a second lock position 146 is formed in a proximal end of the inner edge 128d. This inner edge 128e is linked to the inner edge 128f extending leftward at a predetermined position. Furthermore, the second lock position 146 is set in a space slightly shifted leftward and in the proximal end direction of the substantially triangular space, including the inner edge 128b, the inner edge 128f, and an inner edge 128g.

Basically, in the guiding path structure 122 formed in the aforementioned shape, the second guiding path 123B does not obstruct the movement of the second protrusion 121B. The combination of the first and second guiding paths 123A, 123B forms the distal-end-directional path 150 and the proximal-end-directional path 152. Furthermore, the second guiding path 123B is formed with the inner edge 128f serving as the regulating portion that inhibits the cam structure 120 disposed in the first and second lock positions 136, 146 from moving in the distal end direction with respect to the outer cylinder 48A.

The medical device assembled body 10A (the cam structure 120 and the guiding path structure 122) according to the second embodiment is basically configured as described above. Hereinafter described are movements and effects of the cam structure 120 and the guiding path structure 122 in using the medical device assembled body 10A.

The medical device assembled body 10A advances a syringe 12 under an operation of a user and moves the cam structure 120 along the distal-end-directional path 150 of the guiding path structure 122 of the outer cylinder 48A. In this case, as shown in FIGS. 12A and 12B, the cam structure 120 (the first protrusion 121A, the second protrusion 121B) disposed at the first and second initial positions 130, 140 moves along the distal-end-directional path 150 of the guiding path structure 122.

As shown in FIGS. 12C and 12D, the first protrusion 121A moving along the first initial path 131 makes the first elastic member 124A deform elastically in a direction apart from the inner edge 126a so as to pass through the narrowed portion 150a. At this time, the first protrusion 121A formed in the cylindrical shape smoothly passes between the inner edge 126a and the one-edge portion 125a. After the passage of the first protrusion 121A, the first elastic member 124A elastically reverts to the first state, restoring the width of the narrowed portion 150a to the original width.

When passing through the narrowed portion 150a, the cam structure 120 moves to the first and second junction positions 132, 142 and further passes through the first and second intermediate paths 133, 143, as shown in FIGS. 13A and 13B, thereby proceeding to the first and second positions for puncture 134, 144. Accordingly, a needle 16 is exposed from a distal end-opening 70a of the outer cylinder 48A so that a patient is punctured and subsequently administered with a drug solution.

After puncturing with the needle 16, the cam structure 120 moves from the first and second positions for puncture 134, 144 through the proximal-end-directional path 152 to the first and second lock positions 136, 146. At this time, since the first elastic member 124A narrows the narrowed portion 150a, the cam structure 120 is prevented from moving to the first and second initial paths 131, 141.

As shown in FIGS. 13C and 13D, passing through the first and second junction positions 132, 142, the cam structure 120 moving along the proximal-end-directional path 152 rotates along the inclined shape of the inner edge 126c and proceeds to the narrowed portion 152a. In the narrowed portion 152a, the second elastic member 124B elastically deforms to the right and allows the first protrusion 121A to pass therethrough. The second elastic member 124B elastically restores to the original position after passing through the first protrusion 121A.

Thereafter, as shown in FIGS. 14A and 14B, the cam structure 120 moves to the first and second lock positions 136, 146 in accordance with the shape of the first final path 135. When the cam structure 120 stops moving, the needle 16, body 18, and inner cylinder 44A stop receding relative to the outer cylinder 48A, thereby the needle 16 is housed inside the outer cylinder 48A.

In the first and second lock positions 136, 146, the inner edge 128f of the second guiding path 123B is opposing to a distal end of the second protrusion 121B. As shown in FIGS. 14C and 14D, even when the inner cylinder 44A tries to move in the distal end direction with respect to the outer cylinder 48A, the second protrusion 121B of the inner cylinder 44A is caught in the inner edge 128f so that re-exposure of the needle 16 is firmly inhibited. On the right of the first lock position 136, the proximal end portion 125c of the second elastic member 124B is positioned so as to inhibits rotation of the inner cylinder 44A with respect to the outer cylinder 48A. Therefore, the engagement between the cam structure 120 and the inner edge 128f can be maintained.

As described above, the medical device assembled body 10A according to the second embodiment can also obtain effects similar to those of the medical device assembled body 10 according to the first embodiment. Particularly, the medical device assembled body 10A includes the first and second elastic members 124A, 124B so that it is possible to design elastic force to be applied to the cam structure 120 in each of the distal-end-directional path 150 and the proximal-end-directional path 152. For example, as the elastic force of the first elastic member 124A is designed to be stronger, it is possible to puncture with the needle 16 to a sufficient depth at a breath due to back action caused by the passage of the cam structure 120. Although the first and second elastic members 124A, 124B herein are provided to the first peripheral wall 127, it should be noted that the first elastic member 124A may be provided to the second peripheral wall 128, and the second elastic member 124B may be separately provided to the first peripheral wall 127. In this case, a distal-end-directional-path narrowed portion having a width narrower than that of the second protrusion 121B in the distal-end-directional path 150 is formed between the first elastic member 124A or the distal-end-directional-path elastically-deformable portion and the inner edge 126a of the first peripheral wall 127 or the edge of the distal-end-directional path 150. The first elastic member 124A or the distal-end-directional-path elastically-deformable portion elastically deforms so as to increase the width of the distal-end-directional-path narrowed portion upon contacting with the second protrusion 121B or the cam structure 120, whereby allowing the cam structure 120 to move from the initial position to the puncture position and preventing the cam structure 120 from moving from the puncture position to the initial position.

Third Embodiment

Hereinafter, a medical device assembled body 10B according to a third embodiment will be described with reference to FIGS. 15 to 18C. The medical device assembled body 10B differs from the medical device assembled bodies 10, 10A according to the first and second embodiments in that it is configured to cover a needle 16 and the entire part of a body 18 by a protection device 14B. A hard cover 21A harder than a cap 21 is attached to the outside of the cap 21. It should be noted that the medical device assembled body 10B may be provided with the protection device 14B attached to a syringe 12, or may be provided only with the protection device 14B which is to be attached to the syringe 12 pre-filled with a drug solution (see FIG. 15).

An inner cylinder 44B of the protection device 14B is formed into a relatively large tubular shape that surrounds a barrel body 22 of a body 18. As shown in FIG. 16, the inner cylinder 44B can be divided into a proximal end-tubular portion 162 and a distal end-annular portion 164. The proximal end-tubular portion has an insertion hole 160 slightly larger in diameter than an outer diameter of the body 18 and formed to have a predetermined axial length. The distal end-annular portion 164 is disposed in a distal end of the proximal end-tubular portion 162 and formed to have an outer diameter equivalent to that of the proximal end-tubular portion 162. The proximal end-tubular portion 162 contacts with a hook portion 26 disposed in a side closer to its proximal end and supports the distal end-annular portion 164 at a position apart from the hook portion 26 by a predetermined interval.

The distal end-annular portion 164 is disposed so as to be rotatable relative to the body 18 and the proximal end-tubular portion 162. Accordingly, when an outer cylinder 48B advances with respect to the inner cylinder 44B, the distal end-annular portion 164 rotates and the proximal end-tubular portion 162 does not rotate so that friction can be reduced during the rotation of the inner cylinder 44B. A step 166 serving as a base on which a proximal end portion of a spring 46 is disposed is formed at a distal end of the distal end-annular portion 164. A pair of protrusions (a first protrusion 60A, and a second protrusion 60B) is provided as a cam structure 66 in a side periphery of the distal end-annular portion 164. In the inner cylinder 44B, when the cam structure 66 is guided by the outer cylinder 48B upon puncturing with the needle 16, the distal end-annular portion 164 having a small contact area with a side wall 22a of the body 18 mainly rotates with respect to the body 18.

On the other hand, the outer cylinder 48B of the protection device 14B is formed in a cylindrical shape having a proximal end portion disposed at an intermediate position of the barrel body 22, extending from the proximal end portion in a distal end direction longer than a tip of the needle 16. The outer cylinder 48B includes a proximal end section 168 disposed closer to its proximal end; and a distal end section 170 disposed closer to its distal end than the proximal end section 168. The proximal end section 168 forms a hollow portion 70 having a diameter slightly larger than an outer diameter of the inner cylinder 44B, while the distal end section 170 forms a hollow portion 70 having a diameter smaller than that of the proximal end section 168 and slightly larger than an outer diameter of the barrel body 22. In other words, a step 172 is formed at a boundary of the proximal end section 168 and the distal end section 170 in an inner side of the outer cylinder 48B. As shown in FIG. 17B, the step 172 is a base on which a distal end portion of the spring 46 is disposed.

First and second guiding paths 82A, 82B are formed as a guiding path structure 80 in the proximal end section 168 of the outer cylinder 48B. The guiding path structure 80 is formed in a shape similar to that in the first embodiment and guides the cam structure 66.

A cover 50A of the protection device 14B is formed to be thicker than the outer cylinder 48B, set to have an overall length somewhat longer than an axial length of the body 18. The cover 50A includes a main body 174, a hook portion 188, and a proximal end-annular portion 186 formed in an integrated manner. The main body 174 has a housing space 174a capable of covering the inner cylinder 44B and the outer cylinder 48B. The hook portion 188 is protruded outward in a radial direction, disposed in a proximal end of the main body 174. The proximal end-annular portion 186 is connected to a proximal end of the hook portion 188. Note that a detachable member 178 for detaching the cap 21 and the hard cover 21A is attached to a distal end of the hard cover 21A of the syringe 12 when mounting the protection device 14B (see FIG. 17A).

The main body 174 of the cover 50A has a large diameter portion 180 and a small diameter portion 182. The large diameter portion 180 is substantially as long as the overall length of the body 18. The small diameter portion 182 is formed slightly thinner than the large diameter portion 180, disposed at a distal end of the large diameter portion 180, and protruded in the distal end direction. A distal end-opening 174b communicating with the housing space 174a is formed in the small diameter portion 182. A step 184 which is a boundary of the large diameter portion 180 and the small diameter portion 182 is located in the vicinity of the boundary of the proximal end section 168 and the distal end section 170 of the outer cylinder 48B when the body 18 is attached. The step 172 between the proximal end section 168 and the distal end section 170 is caught in the step 184 of the cover 50A so that the outer cylinder 48B can be prevented from detaching from the distal end-opening 174b of the cover 50A.

In an inner surface of the proximal end-annular portion 186 of the cover 50A, there is provided a locking rib 186a (see FIG. 17B) slightly protruded inward in the radial direction. When the syringe 12 is inserted into the cover 50A, the hook portion 26 passes over the locking rib 186a so as to engage with the hook portion 26 and to fix the syringe 12 and the protection device 14B.

The medical device assembled body 10B according to the third embodiment is basically configured as described above, and its function effect will now be described.

As shown in FIGS. 17B and 18A, in the protection device 14B of the medical device assembled body 10B, the distal end section 170 of the outer cylinder 48B housed in the cover 50A is exposed from the distal end-opening 174b before puncturing with the needle 16. At this time, the cam structure 66 of the inner cylinder 44B is disposed in first and second initial positions 90, 100 of the guiding path structure 80 of the outer cylinder 48B. As a user brings the distal end section 170 of the outer cylinder 48B into contact with the skin of a patient, fixing the distal end section 170 simply and pushing the cover 50A in the distal end direction, the syringe 12 and the inner cylinder 44B advance together with the cover 50A relative to the outer cylinder 48B.

When the cam structure 66 is guided by the guiding path structure 80 of the outer cylinder 48B, the distal end-annular portion 164 rotates. Since configurations and movements of the cam structure 66 and the guiding path structure 80 are similar to those in the first embodiment, the description thereof will be omitted. As shown in FIG. 18B, when the outer cylinder 48B recedes relative to the cover 50A, the needle 16 is exposed from a distal end of the outer cylinder 48B, and the patient is punctured with the needle 16. At this time, the cam structure 66 moves to first and second positions for puncture 94, 106.

After puncturing with the needle 16, the plunger 20 is operated to inject the drug solution into the patient, thereby the medical device assembled body 10B is pulled away from the patient. Accordingly, as shown in FIG. 18C, the inner cylinder 44B, syringe 12, and cover 50A recede with respect to the outer cylinder 48B by biasing force of the spring 46. At this time, the cam structure 66 moves to first and second lock positions 96, 108 of the guiding path structure 80. After puncturing, the movement in a rotative direction and in the distal end direction is prevented by an elastic member 84 of the guiding path structure 80 and an inner edge 74g of a second peripheral wall 74 forming the second lock position 108. Accordingly, the medical device assembled body 10B prevents re-exposure of the needle 16.

As described above, the medical device assembled body 10B according to the third embodiment can also obtain effects similar to those of the medical device assembled body 10 according to the first embodiment. In particular, the protection device 14B according to the third embodiment houses the body 18 so that the user can use the protection device 14B as if to handle the syringe 12. Furthermore, the protection device 14B can be used while it is not only attached to the body 18 but also houses the syringe 12 pre-filled with the drug solution in a manufacturing process, which expands the versatility.

Fourth Embodiment

Hereinafter, a medical device assembled body 10C according to a fourth embodiment will be described with reference to FIGS. 19A to 20C. The medical device assembled body 10C according to the fourth embodiment differs from the medical device assembled bodies 10, 10A, and 10B according to the first to third embodiments in that a protection device 14C is provided with an elastic member 192 and an inner edge 196d (regulating portion) in one guiding path 190. Accordingly, a guiding path structure 191 may have only one guiding path 190 in a peripheral wall 196 of an outer cylinder 48C, or may have a plurality (for example, a pair) of guiding paths 190. A cam structure 120 (protrusion 121) provided to an inner cylinder 44A (see FIG. 11A) of the medical device assembled body 10C is formed in a cylindrical shape as similar to the second embodiment.

The guiding path 190 includes the elastic member 192 extending in a distal end direction from a flanged portion 78 of the outer cylinder 48C, having a lock position 194 on the left of the elastic member 192. In a distal end of the lock position 194, the guiding path 190 includes the inner edge 196d (regulating portion) opposing the cam structure 120.

The elastic member 192 includes a rod portion 198 extending linearly to have a predetermined length; and a tilting portion 200 formed in a shape of an arrow, provided to a distal end of the rod portion 198. An initial path 202 is formed between a one-edge portion 200a on the right of the tilting portion 200 (a part closer to an initial position) and an inner edge 196a of the peripheral wall 196 of the outer cylinder 48C. An intermediate path 204 linearly extends between an inner edge 196b and an inner edge 196c from a position slightly shifted in the distal end direction and leftward (circumferential direction) of the tilting portion 200. Furthermore, a final path 206 is formed between a one-edge portion 200c on the left of the tilting portion 200 (a part closer to the lock position) and the inner edge 196c of the peripheral wall 196 of the outer cylinder 48C. In other words, the elastic member 192 includes both an elastically-deformable portion in a proximal-end-directional path and an elastically-deformable portion in a distal-end-directional path.

A distal-end-directional path 208 includes the initial path 202 and the intermediate path 204 and is formed with a narrowed portion 208a (a distal-end-directional-path narrowed portion) having a width smaller than that of the protrusion 121 of the inner cylinder 44, provided between a distal end-vertex 200b of the tilting portion 200 and the inner edge 196a (see FIG. 19B). A proximal-end-directional path 210 includes the intermediate path 204 and the final path 206 and is formed with a narrowed portion 210a (a proximal-end-directional-path narrowed portion) having a width smaller than that of the protrusion 121 of the inner cylinder 44, provided between the inner edge 196c of the peripheral wall 196 and the one-edge portion 200c of the tilting portion 200.

The lock position 194 is formed by inner edges 196d, 196e, 196f of the peripheral wall 196. The inner edge 196d is recessed, tracing a circular arc in the distal end direction, and serving as a guiding portion that guides the protrusion 121 in a direction apart from the elastic member 192. On the other hand, the inner edge 196f is recessed from the vicinity of the one-edge portion 200c of the tilting portion 200, tracing a circular arc shape in the proximal end direction. A distal end portion of the inner edge 196f serves as a proximal-end-directional-path rotation-inducing portion that guides the protrusion 121 to the lock position 194.

As shown in FIG. 19A, in the medical device assembled body 10C configured as described above, the protrusion 121 is disposed at the initial position 212 before puncturing with the needle 16. When the needle 16 advances and the outer cylinder 48C recedes under an operation of a user, the protrusion 121 moves from the initial position 212 to the initial path 202. When the protrusion 121 passes through the narrowed portion 208a, the elastic member 192 elastically deforms to the left as shown in FIG. 19B, allowing the passage of the protrusion 121. Thereafter, when the needle 16 is inserted into a patient, the protrusion 121 moves to a puncture position 214 through the intermediate path 204 as shown in FIG. 19C.

After puncturing with the needle 16, the outer cylinder 48C advances so that the protrusion 121 recedes from the puncture position 214 and moves along proximal-end-directional path 210 as shown in FIG. 20A. When the protrusion 121 passes through the narrowed portion 210a, the elastic member 84 elastically deforms to the right. Accordingly, the protrusion 121 moves to the lock position 194 as shown in FIG. 20B.

As shown in FIG. 20C, at the lock position 194, the inner edge 196d is disposed in the distal end direction of the protrusion 121, opposing the protrusion 121. Therefore, the protrusion 121 is firmly prevented from moving in the distal end direction, which prevents re-exposure of the needle 16. Furthermore, even when the outer cylinder 48C moves in a rotative direction, the protrusion 121 comes into contact with the one-edge portion 200c of the tilting portion 200 and the rotation is inhibited so that the protrusion 121 can be preferably prevented from being detached.

As described above, the medical device assembled body 10C according to the fourth embodiment can also obtain effects similar to those of the medical device assembled body 10 according to the first embodiment. Moreover, the medical device assembled body 10C can smoothly guide the protrusion 121 from the initial position 212 to the lock position 194 by one guiding path 190 and firmly prevent the protrusion 121 from being detached from the lock position 194. Therefore, for example, as the medical device assembled body 10C is provided with a plurality of guiding paths 190 having the same shape, and each of them is configured to guide the protrusion 121, it is possible to inhibit the re-exposure of the needle 16 more firmly.

While certain embodiments are described above, it should be noted that the present invention is not restricted to the aforementioned embodiments and can be variously modified without departing from the gist of the present invention. For example, a protection device 14, 14A to 14C may be attached to an injection needle mounted on a distal end of a Luer syringe. In this case, an inner member (inner cylinders 44, 44A, and 44B) is rotatably mounted on a needle hub of the injection needle. Furthermore, a needle tip may be exposed from an outer cylinder 48, 48A to 48C with a cam structure 66, 120 disposed at an initial position. In other words, the outer cylinder 48, 48A to 48C may cover at least a part of a needle 16 and the inner member (the inner cylinders 44, 44A, and 44B) before puncturing.

What is claimed is:

1. A protection device configured to be attached to a medical device that comprises a needle having a needle tip at a distal end thereof, and a needle holder holding the needle, the protection device being configured to cover the needle tip after puncturing a target of puncture with the needle, the protection device comprising:
    an inner member disposed so as to be rotatable around the medical device in a circumferential direction, the inner member comprising a cam structure that comprises at least one protrusion that protrudes outward in a radial direction;
    an outer cylinder configured to cover the inner member and at least a part of the needle before puncturing; and
    a biasing member configured to bias the outer cylinder with respect to the inner member in a distal end direction,
    wherein the outer cylinder comprises a guiding path structure that comprises at least one guiding path,
    wherein the cam structure is located in the at least one guiding path, and the at least one guiding path is configured to cause the inner member to rotate in accordance with relative movement of the outer cylinder,
    wherein the outer cylinder is configured to:
        move relative to the inner member in a proximal end direction at a time of puncturing so as to expose the needle tip, and
        move relative to the inner member in the distal end direction after puncturing, due to a biasing force of the biasing member, so as to cover the needle tip,
    wherein the guiding path structure comprises:
        an initial position, where the cam structure is disposed before puncturing,
        a puncture position located distal of the initial position, where the cam structure is to move at the time of puncturing,
        a lock position located proximal of the puncture position, where the cam structure is to move after puncturing,
        a distal-end-directional path configured to guide the cam structure from the initial position to the puncture position at the time of puncturing,
        a proximal-end-directional path configured to guide the cam structure from the puncture position to the lock position after puncturing,
        a proximal-end-directional-path elastically-deformable portion that forms a proximal-end-directional-path narrowed portion together with an edge of the proximal-end-directional path in a middle region of the proximal-end-directional path, the proximal-end-directional-path narrowed portion having an initial width smaller than a width of the protrusion, the proximal-end-directional-path elastically-deformable portion being configured to deform elastically upon contact with the protrusion so as to increase a width of the proximal-end-directional-path narrowed portion and allow the cam structure to move from the puncture position to the lock position,
        a proximal-end-directional-path rotation-inducing portion that is configured to induce the inner member to rotate relative to the outer cylinder by contacting the cam structure when the protrusion passes over the proximal-end-directional-path narrowed portion path and moves to the lock position due to the biasing force of the biasing member, and
        a regulating portion that located at a position different from the proximal-end-directional-path elastically-deformable portion, the regulating portion being configured to inhibit movement of the cam structure in the distal end direction with respect to the outer cylinder by engaging with the cam structure when the cam structure is disposed in the lock position,
    wherein the proximal-end-directional-path elastically-deformable portion is configured to inhibit rotation of the inner member with respect to the outer cylinder by contacting the cam structure when the cam structure moves from the lock position toward the proximal-end-directional-path narrowed portion.

2. The protection device according to claim 1, wherein the proximal-end-directional-path elastically-deformable portion is elastically deformable by contacting the protrusion so as to allow the protrusion to pass through the proximal-end-directional-path narrowed portion substantially linearly along an axis of the outer cylinder.

3. The protection device according to claim 2, wherein the proximal-end-directional path is configured to guide the cam structure so as to allow the cam structure to move substantially linearly along the axis of the outer cylinder from the puncture position to the proximal-end-directional-path rotation-inducing portion.

4. The protection device according to claim 3, wherein the guiding path structure further comprises a distal-end-directional-path rotation-inducing portion located at a middle region of the distal-end-directional path, the distal-end-directional-path rotation-inducing portion being configured to induce the inner member to rotate relative to the outer cylinder by contacting the cam structure when the cam structure moves from the initial position to the puncture position.

5. The protection device according to claim 1, wherein the outer cylinder includes exactly one proximal-end-directional-path elastically-deformable portion.

6. The protection device according to claim 1,
    wherein the at least one guiding path comprises a first guiding path and a second guiding path,
    the at least one protrusion comprises a first protrusion configured to move in the first guiding path and a second protrusion configured to move in the second guiding path,
    the proximal-end-directional-path elastically-deformable portion is located in the first guiding path, and
    the regulating portion is located in the second guiding path,
    wherein each of the first guiding path and the second guiding path comprises the initial position, the puncture position, the lock position, the distal-end-directional path, and the proximal-end-directional path.

7. The protection device according to claim 1, wherein the guiding path structure comprises a distal-end-directionalpath elastically-deformable portion that forms a distal-end-directional-path narrowed portion together with an edge of the distal-end-directional path in a middle region of the distal-end-directional path, the distal-end-directional-path narrowed portion having an initial width smaller than a width of the cam structure,
  wherein the distal-end-directional-path elastically-deformable portion is configured to deform elastically upon contacting the cam structure so as to increase the width of the distal-end-directional-path narrowed portion and inhibit the cam structure from moving from the puncture position to the initial position.

8. The protection device according to claim 7, wherein the outer cylinder comprises an elastic member that comprises both the proximal-end-directional-path elastically-deformable portion and the distal-end-directional-path elastically-deformable portion,
  wherein the elastic member is disposed between the initial position and the lock position in a circumferential direction of the outer cylinder, and extends in the distal end direction from a proximal end portion of the outer cylinder.

9. The protection device according to claim 7, wherein the outer cylinder comprises:
  a first elastic member that is disposed in a vicinity of the lock position and comprises the proximal-end-directional-path elastically-deformable portion; and
  a second elastic member that is disposed at a position different from the first elastic member and comprises the distal-end-directional-path elastically-deformable portion.

10. The protection device according to claim 2, wherein the regulating portion comprises a guiding portion that is configured to guide the cam structure disposed in the lock position in a direction away from the proximal-end-directional-path elastically-deformable portion when the outer cylinder moves in the proximal end direction with respect to the inner member while the cam structure is at the lock position.

11. A medical device assembled body comprising:
  the protection device according to claim 1; and
  the medical device, to which the protection device is attached.

12. The medical device assembled body according to claim 11, wherein the medical device is a syringe that comprises:
  a barrel body having a space portion configured to store a liquid in a proximal end of the needle holder, and
  a cap configured to seal the needle tip,
  wherein a syringe is configured to discharge the liquid from the tip of the needle.

13. The medical device assembled body according to claim 12, wherein the inner member is rotatably disposed on an outer periphery of the barrel body,
  the outer cylinder extends from a position where at least a part of the needle is covered to a position where the inner member is covered, and
  the medical device assembled body further comprises a cover that is configured to house the protection device and attach the protection device to the syringe.

14. A protection device configured to be attached to a medical device that comprises a needle having a needle tip at a distal end thereof, and a needle holder holding the needle, the protection device being configured to cover the needle tip after puncturing a target of puncture with the needle, the protection device comprising:
  an inner cylinder disposed so as to be rotatable around the medical device in a circumferential direction, the inner cylinder comprising at least one protrusion that protrudes outward in a radial direction;
  an outer cylinder configured to cover the inner cylinder and at least a part of the needle before puncturing, the outer cylinder comprising a cylindrical peripheral wall and an upper end wall that is linked to a distal end of the peripheral wall and protrudes inward in the radial direction; and
  a coil spring configured to bias the outer cylinder with respect to the inner cylinder in a distal end direction,
  wherein the outer cylinder comprises a guiding path structure that comprises at least one guiding path,
  wherein the at least one protrusion of the inner cylinder is located in the at least guiding path, and the at least one guiding path is configured to cause the inner cylinder to rotate in accordance with relative movement of the outer cylinder,
  wherein the outer cylinder is configured to:
    move relative to the inner cylinder in a proximal end direction at a time of puncturing so as to expose the needle tip, and
    move relative to the inner cylinder in the distal end direction after puncturing, due to a biasing force of the coil spring, so as to cover the needle tip,
  wherein the at least guiding path comprises:
    an initial position, where the at least one protrusion is disposed before puncturing,
    a puncture position located distal of the initial position, where the at least one protrusion is to move at the time of puncturing,
    a lock position disposed proximal of the puncture position, where the at least one protrusion is to move after puncturing,
    a distal-end-directional path configured to guide the at least one protrusion from the initial position to the puncture position at the time of puncturing,
    a proximal-end-directional path configured to guide the at least one protrusion from the puncture position to the lock position after puncturing, and
    at least one rotation-inducing portion that is configured to induce the inner cylinder to rotate relative to the outer cylinder by contacting the at least one protrusion when the at least one protrusion moves from the initial to the locked position,
  wherein the inner cylinder comprises a support base that supports a proximal end of the coil spring,
  wherein the upper base wall of the outer cylinder comprises a proximal end surface that supports a distal end of the coil spring, and
  wherein the coil spring is wound, toward a proximal end of the coil spring, in a direction coinciding with a rotation direction of the inner cylinder during a rotation of the inner cylinder with respect to the outer cylinder caused by movement of the at least one protrusion from the initial position to the locked position.

15. The protection device according to claim 14, wherein the at least one rotation-inducing portion comprises a first rotation-inducing portion in the distal-end-directional path and second rotation-inducing portion in the proximal-end-directional path.

16. The protection device according to claim 14, wherein the inner cylinder further comprises a ring portion that protrudes outward in a radial direction and comprises a distal end surface that constitutes the support base.

17. A Method of using a medical device assembled body, the method comprising:
- providing a medical device that comprises:
  - a needle having a needle tip at a distal end of the needle; and a protection device attached to the medical device, the protection device comprising:
    - an inner member disposed so as to be rotatable around the medical device in a circumferential direction, the inner member comprising a cam structure that comprises at least one protrusion that protrudes outward in a radial direction,
    - an outer cylinder configured to cover the inner member and at least a part of the needle before puncturing the needle tip to a target site, the outer cylinder comprising a guiding path structure that comprises at least one guiding path, wherein the cam structures is located in the at least one guiding path, and the at least one guiding path is configured to cause the inner member to rotate in accordance with relative movement of the outer cylinder, and
    - a biasing member configured to bias the outer cylinder with respect to the inner member in a distal end direction,
    - wherein the cam structure in an initial position and the outer cylinder covers the inner member and at least a part of the needle;
- moving the outer cylinder relative to the inner member in a proximal direction against a biasing force of the biasing member so as to puncture the target site with the needle tip, while moving the cam structure along a distal-end-directional path of the guiding path structure from the initial position to a puncturing position of the guiding path structure that is disposed distal of the initial position; and
- after the puncturing of the needle tip, moving the outer cylinder relative to the inner member in a distal direction by the biasing force of the biasing member so as to cover the needle tip by the outer cylinder, while moving the cam structure along a proximal-end-directional path of the guiding path structure from the puncturing position to a locked position of the guiding path structure that is disposed at proximal of the puncturing position,
- wherein the guiding path structure comprises:
  - a first elastically-deformable portion that forms a first narrowed portion together with an edge of the proximal-end-directional path in a middle region of the proximal-end-directional path, the first narrowed portion having an initial width smaller than a width of the protrusion of the cam structure;
  - a first rotation-inducing portion that is disposed at a proximal end of the proximal-end-directional path, the first rotation-inducing portion being configured to induce the inner member to rotate relative to the outer cylinder by contacting the cam structure; and
  - a regulating portion that is disposed at a position different from the first elastically-deformable portion configured to inhibit movement of the cam structure in the distal end direction with respect to the outer cylinder by engaging with the cam structure when the cam structure is disposed in the lock position,
- wherein during the movement of the cam structure along the proximal-end-directional path, the first elastically-deformable portion is deformed by contacting the protrusion of the cam structure such that a width of the first narrowed portion is increased and the protrusion of the cam structure is allowed to pass over the first narrowed portion,
- wherein after the protrusion of the cam structure has passed over the first narrowed portion, the first elastically-deformable portion is restored to an original state where the width of the first narrowed portion is restored to the initial width, and
- wherein after the movement of cam structure to the locked position, rotation of the inner member with respect to the outer cylinder is inhibited by the first elastically-deformable portion contacting the cam structure in the locked position, while movement of the cam structure in the distal end direction with respect to the outer cylinder is inhibited by the regulation portion engaging with the cam structure disposed in the lock position.

* * * * *